(12) United States Patent
Nagashimada

(10) Patent No.: US 9,414,849 B2
(45) Date of Patent: Aug. 16, 2016

(54) MEDICAL MANIPULATOR SYSTEM

(71) Applicant: Karl Storz GmbH & Co. KG, Tuttlingen (DE)

(72) Inventor: Masaru Nagashimada, Fujinomiya (JP)

(73) Assignee: Karl Storz GmbH & Co. KG, Tuttlingen (DE)

( * ) Notice: Subject to any disclaimer, the term of this patent is extended or adjusted under 35 U.S.C. 154(b) by 0 days.

(21) Appl. No.: 13/626,112

(22) Filed: Sep. 25, 2012

(65) Prior Publication Data

US 2013/0023860 A1 Jan. 24, 2013

Related U.S. Application Data

(63) Continuation of application No. PCT/JP2011/057526, filed on Mar. 28, 2011.

(30) Foreign Application Priority Data

Mar. 30, 2010 (JP) .................................. 2010-076940

(51) Int. Cl.
*A61B 17/00* (2006.01)
*G05B 19/00* (2006.01)
(Continued)

(52) U.S. Cl.
CPC .............. *A61B 17/1626* (2013.01); *A61B 17/00* (2013.01); *G05B 19/00* (2013.01);
(Continued)

(58) Field of Classification Search
CPC ................... A61B 19/22; A61B 19/44; A61B 2017/00398; A61B 2017/0046; A61B 2019/2242; A61B 19/2203; A61B 17/00; B25J 15/04; G05B 19/00; G05B 1/00

USPC .................. 606/1; 901/30; 700/17; 715/771; 388/937

See application file for complete search history.

(56) References Cited

U.S. PATENT DOCUMENTS 5,077,506 A * 12/1991 Krause ............................. 318/71
5,482,209 A * 1/1996 Cochran et al. .............. 236/46 R
(Continued)

FOREIGN PATENT DOCUMENTS

JP          4026494      *  1/1992    ............. D05B 69/18
JP          8-071072 A      3/1996
(Continued)

OTHER PUBLICATIONS

International Search Report (PCT/ISA/210) issued on Apr. 19, 2011, by the Japanese Patent Office as the International Searching Authority for International Application No. PCT/JP2011/057526.
(Continued)

*Primary Examiner* — William Thomson
*Assistant Examiner* — Nathan J Jenness
(74) *Attorney, Agent, or Firm* — Whitmyer IP Group LLC

(57) ABSTRACT

A medical manipulator system includes an operation unit that has motors, a composite input unit and a tip operating unit that is operated by a driving force of the motors, a working unit that may by attached to and detached from the operating unit, and a console. The motors are driven based on an input operation to the composite input unit. The tip operating unit performs at least a rotation operation along an axial direction or a swing operation that crosses the axial direction. The console changes a driving speed of the motors and includes a speed setting unit that changes an operating speed of the rotation operation or the swing operation of the tip operating unit.

19 Claims, 15 Drawing Sheets

(51) Int. Cl.
*A61B 17/16* (2006.01)
*A61B 18/14* (2006.01)

(52) U.S. Cl.
CPC ............. *A61B2017/0046* (2013.01); *A61B 2017/00199* (2013.01); *A61B 2017/00225* (2013.01); *A61B 2018/1422* (2013.01); *A61B 2034/254* (2016.02)

(56) References Cited

U.S. PATENT DOCUMENTS

| | | |
|---|---|---|
| 6,120,433 A | 9/2000 | Mizuno et al. |
| 6,666,860 B1* | 12/2003 | Takahashi ................. 606/34 |
| 2002/0002368 A1* | 1/2002 | Tomita et al. ............. 606/4 |
| 2002/0038102 A1* | 3/2002 | McFarlin ......... A61B 17/1626 604/30 |
| 2002/0087179 A1* | 7/2002 | Culp et al. ................ 606/167 |
| 2003/0093503 A1* | 5/2003 | Yamaki et al. ............ 709/220 |
| 2004/0116906 A1* | 6/2004 | Lipow ...................... 606/1 |
| 2005/0180615 A1* | 8/2005 | Gerder ...................... 382/124 |
| 2005/0222587 A1* | 10/2005 | Jinno et al. ................ 606/130 |
| 2006/0020258 A1* | 1/2006 | Strauss et al. ............. 606/1 |
| 2006/0074405 A1* | 4/2006 | Malackowski et al. ...... 606/1 |
| 2006/0259055 A1* | 11/2006 | Thorne et al. ............. 606/180 |
| 2006/0287645 A1* | 12/2006 | Tashiro et al. ............. 606/1 |
| 2007/0130376 A1* | 6/2007 | Moon ....................... 710/8 |
| 2008/0091072 A1* | 4/2008 | Omori et al. ............. 600/131 |
| 2008/0262476 A1* | 10/2008 | Krause et al. ............. 604/540 |
| 2008/0262654 A1* | 10/2008 | Omori et al. ............. 700/245 |
| 2009/0018390 A1 | 1/2009 | Honda et al. |
| 2009/0030428 A1* | 1/2009 | Omori et al. ............. 606/130 |
| 2009/0110533 A1* | 4/2009 | Jinno ....................... 414/783 |
| 2010/0304932 A1* | 12/2010 | Kolman ............. A63B 71/0619 482/7 |

FOREIGN PATENT DOCUMENTS

| | | |
|---|---|---|
| JP | 2001-276091 A | 10/2001 |
| JP | 2004-105451 A | 4/2004 |
| JP | 2009-011809 A | 1/2009 |
| JP | 2009-226029 A | 10/2009 |

OTHER PUBLICATIONS

Notice of Rejection of Application from Japan, Application No. 2012-508271, Issued: Feb. 17, 2015, 3 pages.

* cited by examiner

MEDICAL MANIPULATOR SYSTEM

CROSS REFERENCES TO RELATED APPLICATIONS

This application is a continuation of International Application No. PCT/JP2011/057526 filed on Mar. 28, 2011 and claims priority to Japanese Patent Application JP2010-076940 filed in the Japanese Patent Office on Mar. 30, 2010, the entire content of both of which is incorporated herein by reference.

TECHNICAL FIELD

The present invention generally relates to a medical manipulator system that includes a main body, a working unit in which a tip operating unit is provided at a tip of a shaft, and a controller that is connected to the main body portion, which drives and controls the tip operating unit.

BACKGROUND DISCUSSION

For example, in endoscopic surgery (also referred to as "laparoscopic surgery"), a plurality of holes are drilled on an abdomen of a patient, after a trocar (cylindrical instrument) is inserted as a passage port of an instrument, a tip of forceps having a shaft is inserted into a body cavity through the trocar, and surgery for the affected part is carried out. Grippers, scissors, and blades of an electrosurgical knife for gripping biological tissues are mounted to the tip of the forceps as a working unit.

As the forceps that are inserted from the trocar, in addition to general forceps that does not have a joint at the working unit of the tip, forceps that have a plurality of joints at the working unit, which are known as a manipulator or manipulator system have been developed. An example is disclosed in Japanese Application Publication No. 2004-105451. The manipulator allows the operation to be performed with a relatively high degree of freedom in the body cavity and the manipulation is relatively easy.

The manipulator has a working unit that includes a tip operating unit (also referred to as an "end effector") provided at the tip of the slender shaft, and an actuator that drives the tip operating unit through a wire is provided at a main body portion (operating unit). The wire is wound around a pulley at a base end side of the main body portion (or operating unit).

In the above-disclosed manipulator, a plurality of joint portions are provided at a tip operating unit, and the tip operating unit can perform a roll-axis operation of carrying out a rotation operation about an axial direction of the tip operating unit, a yaw-axis operation and a pitch-axis operation of carrying out a swing (yawing) operation along a direction that intersects the axial direction based on the drive of the actuator. Relatively high operability can thus be achieved in a body cavity.

However, it is considered that individual differences in the operating speed of the easy to handle tip operating unit are generated according to doctors handling the manipulator and an optimal operating speed may be also different according to a surgical form or a kind of the tip operating unit (for example, gripper, scissors).

SUMMARY

According to one aspect, a medical manipulator includes: a main body portion that includes drive shafts which are rotated by actuators and an input unit which drives the actuators. A working unit includes driven shafts which are rotatably driven by the drive shafts, and a tip operating unit which is operated by the rotation of the driven shafts. A shaft which is provided at a tip of the tip operating unit, and that is attached to and detached from the main body portion, and a controller that is connected to the main body portion and therefore, controls so as to drive the actuators based on an input operation to the input unit, wherein the actuators are driven based on the input operation to the input unit, and therefore, the tip operating unit can perform at least a rotation operation along an axial direction or a swing operation that crosses the axial direction, and the controller changes driving speeds of the actuators, and includes a speed setting unit that can change an operating speed of the rotation operation or the swing operation of the tip operating unit.

According to a further aspect, the controller includes the speed setting unit that can change the operating speed in the tip operating unit in which the rotation operation or the swing operation can be performed, and therefore, according to individual differences of a user (for example, doctor) that handles the manipulator including main body portion and the working unit, or kind of tip operating unit (for example, scissors or needle driver), the setting of the operating speed of the rotation operation or the swing operation can be optimally changed, and high operability can be achieved.

If the tip operating unit can perform the rotation operation and the swing operation and the speed setting unit can individually change the operating speeds of the rotation operation and the swing operation respectively, relative degree of freedom of setting the operating speed of the tip operating unit is improved, and relatively higher operability can be achieved.

If the controller includes a storage unit that stores a set value of the operating speed of the tip operating unit through the speed setting unit, the set speed information is stored and can rather easily be retrieved when needed for use.

The controllers may include a storage unit that stores the values of the operating speed of the tip operating unit set through the speed setting unit, and a combination of the set values of each of the operating speeds of the rotation operation and the swing operation can be registered in a plurality of combinations in the storage unit. Thereby, for example, sets of the set speed information of preferences of a plurality of users can be registered, and even when the plurality of users use the same controller, the set of each person can be rapidly retrieved.

If there are a plurality of kinds of tip operating units, and the speed setting unit can change the operating speed for each kind of the tip operating unit that is provided in the working unit mounted to the main body portion and can register the set value of the operating speed for each kind in the storage unit, the setting and registration of the operating speed which more flexibly correspond to the preference of the user in the operating speed for each kind of the tip operating unit can be performed.

The controller may simultaneously connect a plurality of medical manipulators that include the main body portion and the working unit and may individually change the operating speed of the tip operating unit of each medical manipulator respectively. Thereby, for example, even when a single user simultaneously uses the plurality of manipulators and performs the manipulation, the operating speed of each tip operation unit can be flexibly changed.

If the medical manipulator includes a display portion that displays the set speed of the tip operating unit, the set speed can be specified by the user, and the change of the operating speed can be also rather easily performed.

The controller can include a speed setting unit that can change the operating speed in the tip operating unit in which the rotation operation or the swing operation can be performed. Thereby, according to individual differences of a user (for example, doctor) that handles the manipulator including main body portion and the working unit, or kind of tip operating unit (for example, scissors or needle driver), the setting of the operating speed of the rotation operation or the swing operation can be optimally changed, and high operability can be achieved.

According to another aspect, a medical manipulator system, which includes a main body portion that includes drive shafts which are rotated by actuators and an input unit which drives the actuators, and a working unit that includes driven shafts which are rotatably driven by the drive shafts. A tip operating unit is operated by the rotation of the driven shafts, and a shaft is provided at a tip of the tip operating unit. A controller connected to the main body portion, which controls the actuators based on an input operation to the input unit, and wherein the actuators are driven based on the input operation to the input unit. The tip operating unit performs at least a rotation operation along an axial direction or a swing operation that crosses the axial direction. The controller changes driving speeds of the actuators, and includes a speed setting unit, which changes an operating speed of the rotation operation or the swing operation of the tip operating unit.

According to another aspect, a medical manipulator system, which includes a main body portion that includes drive shafts which are rotated by actuators and an input unit which drives the actuators, and a working unit that includes driven shafts which are rotatably driven by the drive shafts. A tip operating unit is operated by the rotation of the driven shafts, and a shaft is provided at a tip of the tip operating unit. The shaft is attached to and detached from the main body portion. A controller that is connected to the main body portion and controls the actuators based on an input operation to the input unit, and wherein the actuators are driven based on the input operation to the input unit. The tip operating unit performs at least a rotation operation along an axial direction or a swing operation that crosses the axial direction, and the controller changes driving speeds of the actuators, and includes a speed setting unit that changes an operating speed of the rotation operation or the swing operation of the tip operating unit.

The medical manipulator disclosed here is configured to substantially optimize the operating speed of the tip operating unit according to the individual differences of users and the kind of tip operating unit.

DETAILED DESCRIPTION

Set forth below with reference to the accompanying drawings is a detailed description of an embodiment of a medical manipulator disclosed here by way of example.

Figure 1:
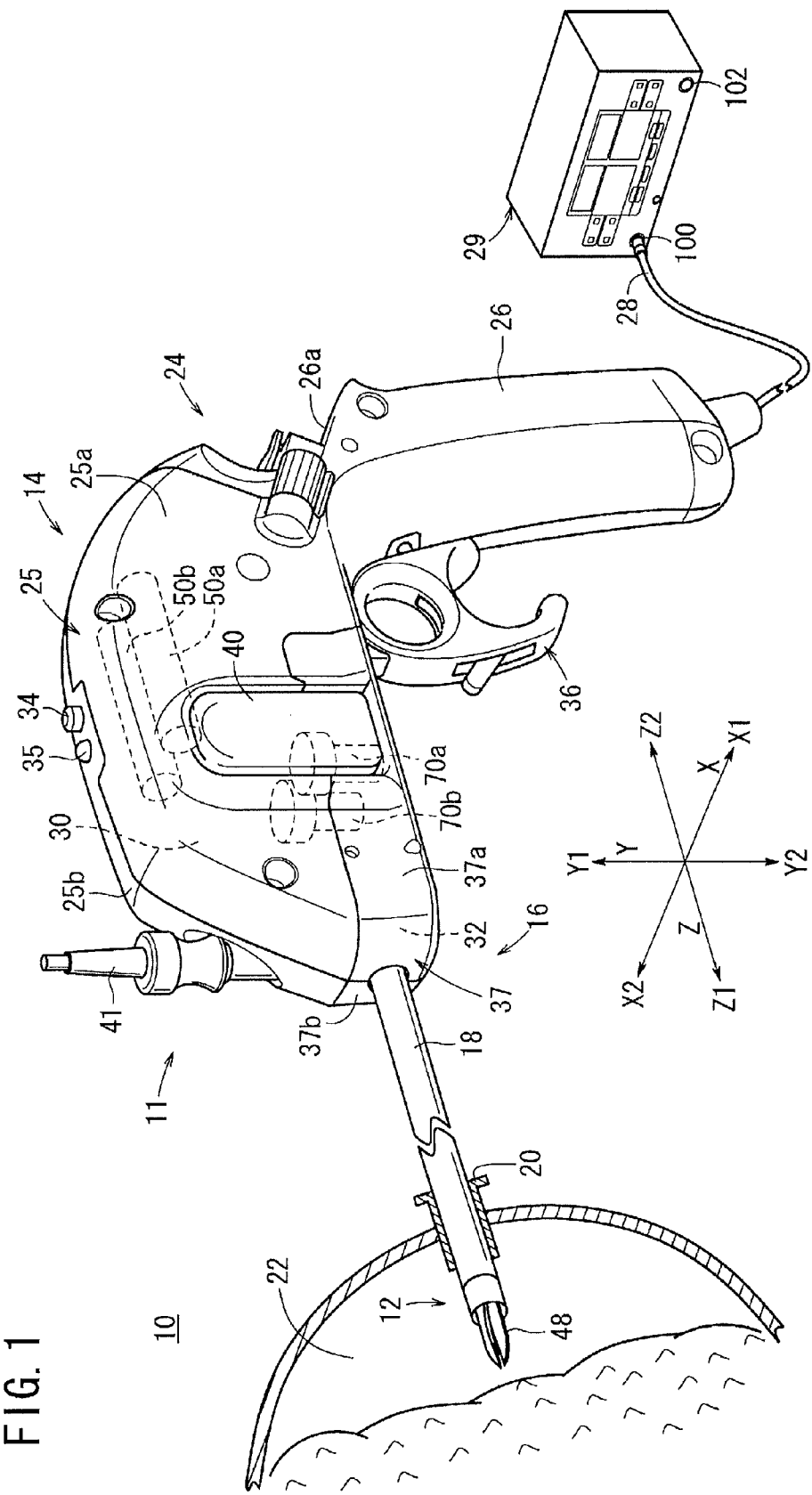
FIG. 1 is an overall view showing a manipulator system according to an embodiment.

As shown in FIG. 1, a manipulator system (medical manipulator system) 10 includes a manipulator (medical manipulator) 11 and a console (controller) 29 that controls of the drive of the manipulator 11. The manipulator 11 is a medical instrument for performing predetermined processes such as a gripping of a portion of a living body, a curved needle, a cutting of a portion of a living body, which is performed by operating a tip operating unit 12 provided at a tip of a shaft 18.

In the descriptions below, in FIG. 1, the width direction is defined as an X direction, the height direction is defined as a Y direction, and the extension direction of the shaft 18 is defined as a Z direction. In addition, when viewed from the tip side, the right side is defined as an X1 direction, the left side is defined as an X2 direction, the up direction is defined as a Y1 direction, the down direction is defined as a Y2 direction, the front side of the shaft 18 is defined as a Z1 direction, and the rear side of the shaft 18 is defined as a Z2 direction. In addition, unless otherwise noted, these direction descriptions are expressed with a case where the manipulator 11 has a reference posture (neutral posture) as a reference. These directions are for convenience of explanation, and it is needless to say that the manipulator 11 can be used in any orientation (for example, with up and down inverted).

The manipulator 11 is gripped and operated by hands and includes an operating unit (main body portion) 14 that accommodates a drive mechanism 30 which applies a driving force to the tip operating unit 12 and a working unit (forceps) 16 that is attached to and detached from the operating unit 14, a cable 28 that extends from a lower end of a grip handle 26 is connected to the console 29, and therefore, the manipulator system 10 is configured.

Figure 2:
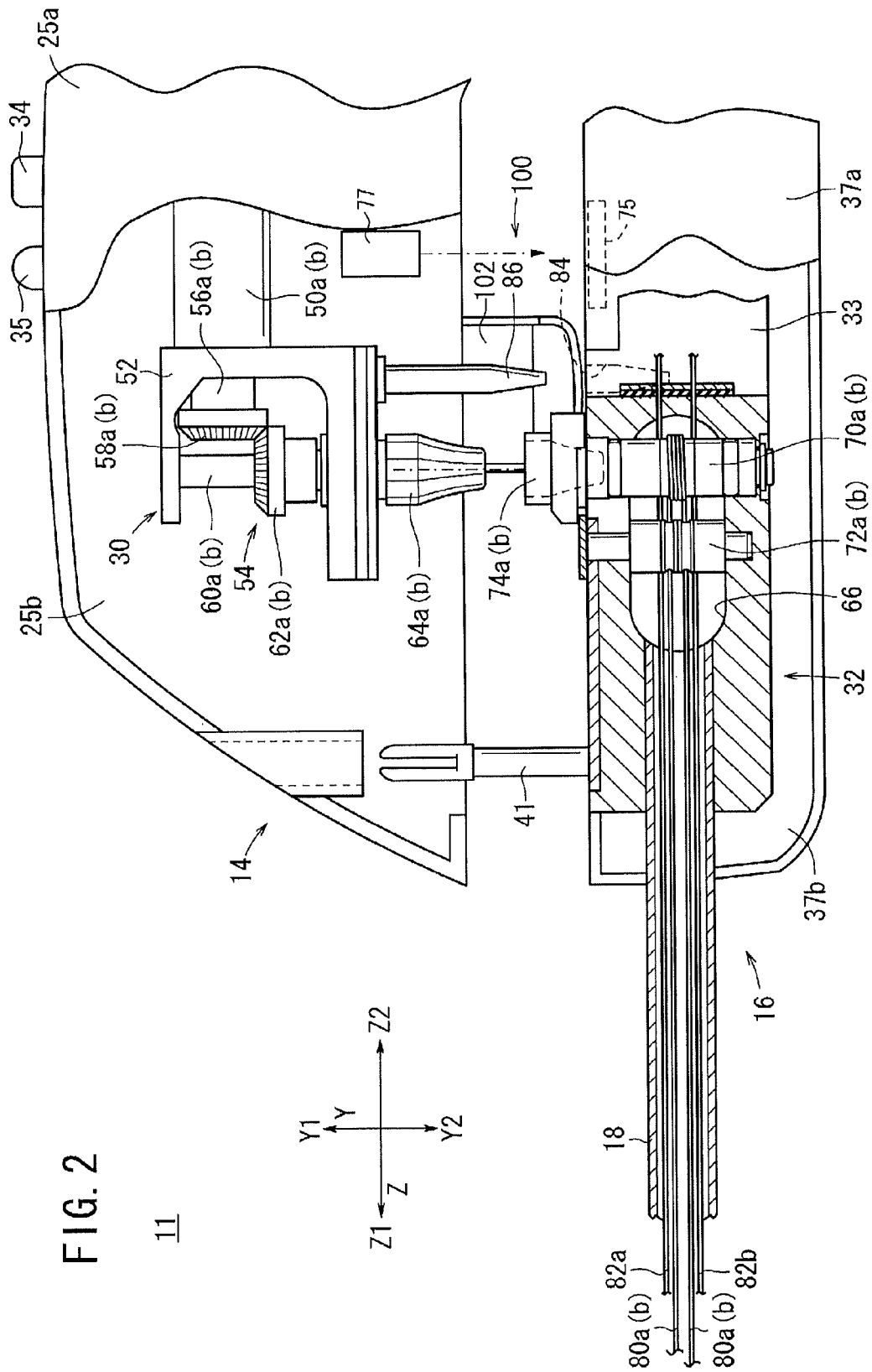
FIG. 2 is a partial cross-sectional side view of a manipulator in a state where a working unit and an operating unit are separated from each other.

As shown in FIGS. 1 and 2, the operating unit 14 is configured in an approximate L shape that extends in the Z1 direction and Y2 direction and includes a pair of upper covers 25a and 25b that is approximately symmetrically divided in the Z direction (hereinafter, collectively referred to as an "upper cover 25") as a housing, the drive mechanism 30 is positioned in the inner portion of the housing, and a portion of the operating unit that extends in the Y2 direction at the base end side is configured of the grip handle 26 that is gripped by hands. The grip handle 26 has a length that is suitable to be gripped by hands, and a composite input unit (input unit) 24 is provided on an inclined plane 26a of the upper portion of the grip handle.

A master switch 34 is provided so as to be exposed from the upper cover 25b in the vicinity of the top in the Y1 direction of the operating unit 14, and a LED 35 is provided at a place which is rather easily observed in the Z1 direction of the master switch 34. In FIG. 1, an electrode plug 41 that extends from the vicinity of the end in the Z1 direction of the operating unit 14 to the Y1 direction is an electrode to which a high voltage source is connected when the manipulator 11 is used as an electronic scalpel, and the electrode plug can supply a high voltage to the tip operating unit 12 side through a conducting structure (not shown).

Figure 3:
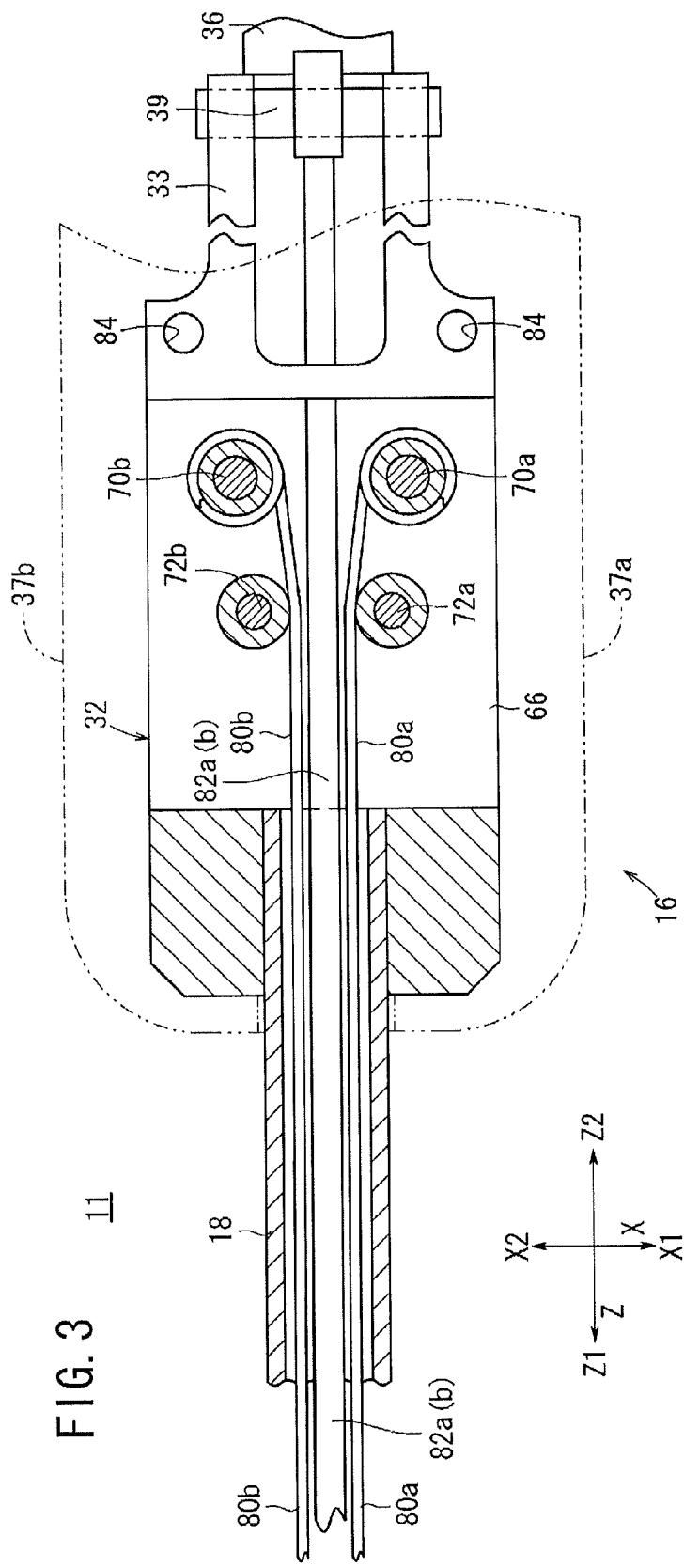
FIG. 3 is a cross-sectional plan view in which a portion of the working unit is omitted.

As shown FIGS. 1 to 3, the working unit 16 includes the tip operating unit 12 that performs a work, the shaft 18 that installs the tip operating unit 12 on the tip and is long and hollow, a pulley box 32 to which the base end side of the shaft 18 is fixed, and a trigger lever 36 that is pivotally supported to a trigger lever support portion 33 which extends from the end in the Z2 direction of the pulley box 32. The work unit 16 includes a pair of lower covers 37a and 37b (hereinafter, collectively referred to as a "lower cover 37") that is approximately symmetrically divided in the Z direction as a housing, and the pulley box 32 is accommodated in the inner portion of the working unit. The trigger lever support portion 33 is a pair of plates that extends so as to be parallel in the Z2 direction from the Z2 side end surface of the pulley box 32 and rotatably and pivotally supports the trigger lever 36 through a trigger shaft 39 that crosses between the plates (refer to FIG. 3).

As shown in FIG. 1, the tip operating unit 12 and the shaft 18 are configured so as to have a small diameter, can be inserted into a body cavity 22 from a cylindrical trocar 20 that is provided at abdomen of a patient, and can perform various kinds of manipulation such as excision of an affected part, gripping, suture, and ligation in the body cavity 22 through the operation of the composite input unit 24 and the trigger lever 36.

Figure 4:
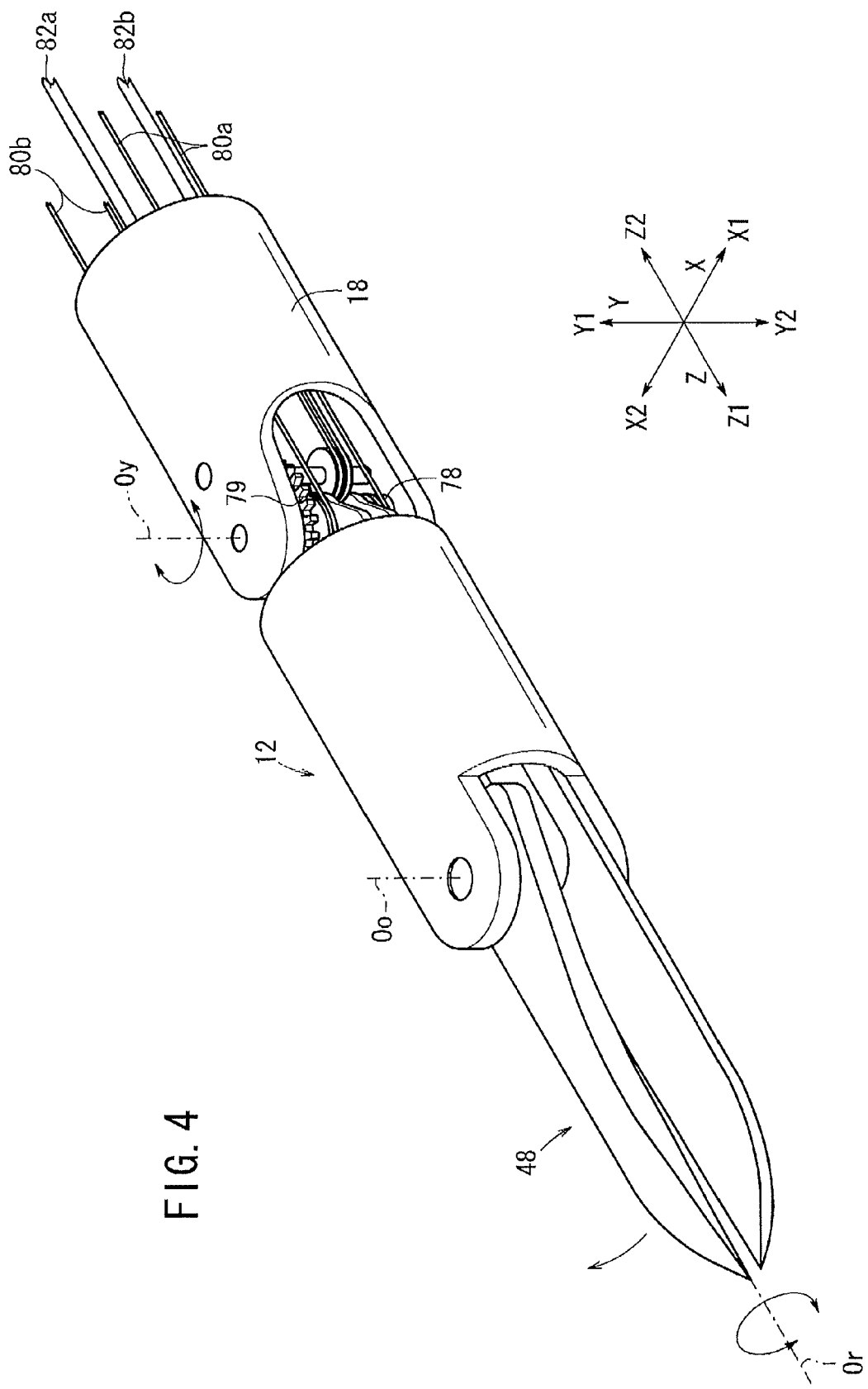
FIG. 4 is a perspective view of a tip operating unit.

For example, as shown in FIG. 4, the tip operating unit 12 that is operated based on the operation of the composite input unit 24 and the trigger lever 36 includes scissors 48, and can perform a three-axis operation including a yaw axis Oy operation that tilts based on the Y axis, a roll axis Or operation that rotates based on an axis (Z axis at the time of neutral posture) that is oriented toward the tip, and an opening and closing axis Oo operation that opens and closes the scissors 48. In the case of the present embodiment, the yaw axis Oy and the roll axis Or are electrically driven based on the operation of the composite input unit 24 and the opening and closing axis Oo is mechanically driven based on the operation of the trigger lever 36. Along with the yaw axis Oy, or instead of the yaw axis Oy, a pitch-axis operation that swings the tip operating unit 12 up and down may be applied. Here, mechanical driving means a method that is driven via a wire, a chain, a timing belt, a link, a rod, a gear, and is a method that is mainly driven via mechanical components, which are made of a non-elastic solid, in a power transmission direction. Some inevitable extension may be generated due to the tension in the wire, the chain, however, these are regarded as mechanical components made of a non-elastic solid.

The working unit 16 is connected and fixed to the operating unit 14 by a pair of left and right detachable levers 40 and 40 that are provided in the operating unit 14 and can be detached from the operating unit 14 through the opening operation of the detachable lever 40, and therefore, replacement work can be rather easily performed at a surgery site without using specific equipment.

Figure 5:
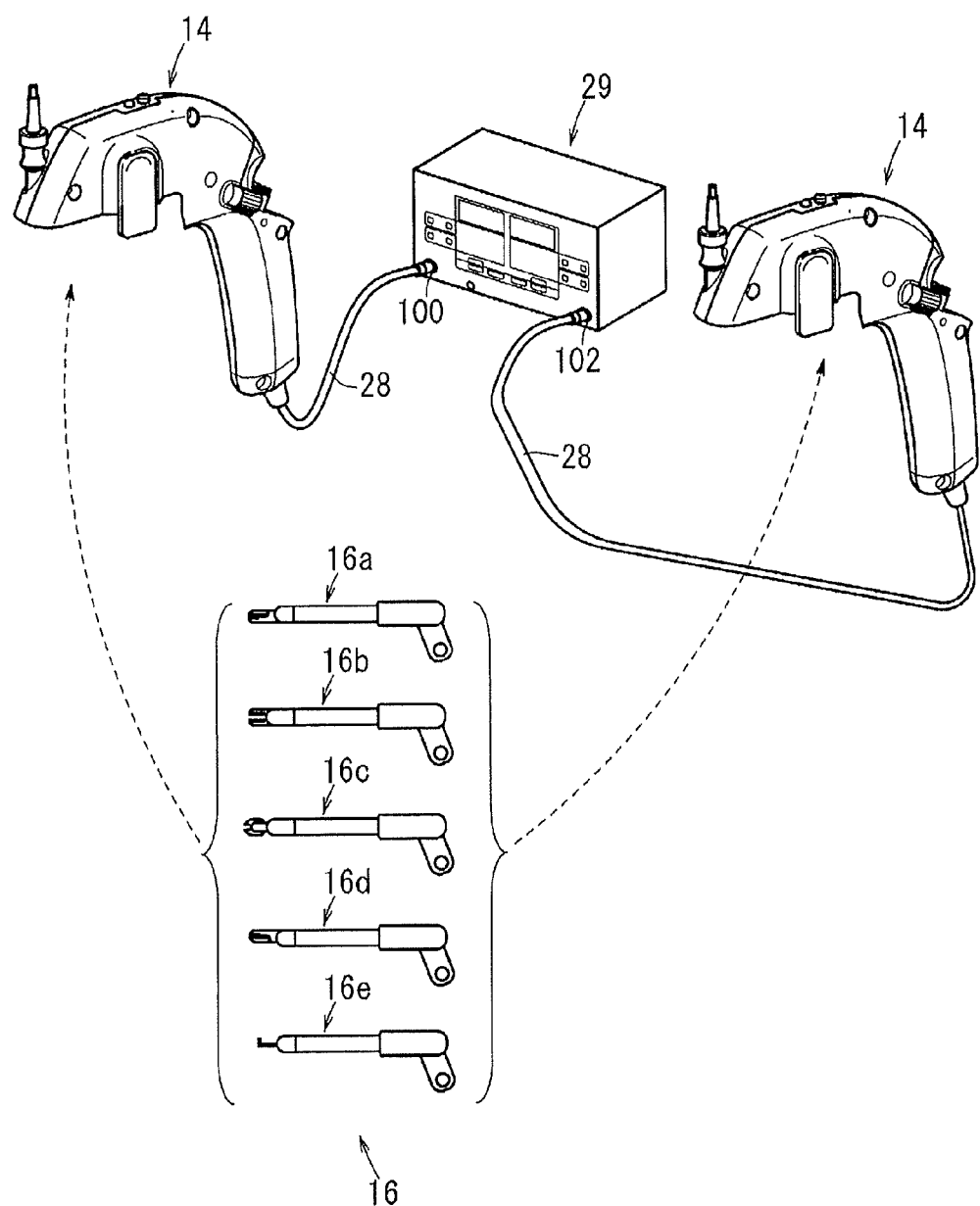
FIG. 5 is an explanatory diagram of combinations of the manipulator.

Here, as shown in FIG. 5, the manipulator 11 and the manipulator system 10 including the manipulator 11, can selectively adopt various configurations. For example, in the working unit 16 that is attached to and detached from the operating unit 14, five kinds of working units 16a, 16b, 16c, 16d, and 16e, in which the kind of the tip operating unit 12 is changed as a variation, are prepared.

Two manipulators 11 can be simultaneously connected to the console 29. That is, a first connector 100 and a second connector 102 are provided in the console 29, single operating unit 14 can be mounted to each of the connectors 100 and 102 respectively. In addition, for example, a desired working unit among the above-described five kinds of working units 16a to 16e can be mounted to each operating unit 14. Thereby, a practitioner simultaneously uses two manipulators according to a kind of manipulation, or a practice, which selectively combines various working units 16a to 16d as the working unit 16, and can configure the manipulator system 10.

For example, as the kind of the tip operating unit 12, there may be scissors, a gripper, a needle driver (grip forceps), an electronic scalpel, a blade type electronic scalpel, or a hook type electronic scalpel. Each of the working units 16a to 16e in which each kind of the tip operating units 12 is provided has a common configuration including the pulley box 32 from the shaft 18 to the trigger lever 36. However, identification information such as the type of the working units can be supplied to the operating unit 14 side, that is, the console 29 by a bar code 75 described below.

The drive mechanism 30 and the pulley box 32 can be attached to and detached from each other, and therefore, a driving force can be transmitted from the operating unit 14 to the working unit 16.

As shown in FIGS. 1 and 2, the drive mechanism 30 includes two motors (actuator) 50a and 50b that are lined up in the X direction, a bracket 52 that supports the motors 50a and 50b, and a gear mechanism portion 54 that converts the rotation direction of the motors 50a and 50b and transmits the driving force to the working unit 16 side.

The motors 50a and 50b have a columnar form, output shafts 56a and 56b that are decelerated by a reduction gear (not shown) penetrate one surface of the bracket 52, and driving bevel gears 58a and 58b configuring the gear mechanism portion 54 is fixed to the output shafts 56a and 56b. For example, the motors 50a and 50b are a DC motor, and a rotary encoder which is an angle sensor (not shown) are provided in the motors.

The gear mechanism portion 54 is provided in a space within the bracket 52, and includes two drive shafts (drive axes) 60a and 60b that are lined up in the X direction and two driven bevel gears 62a and 62b that are fixed to each of drive shafts 60a and 60b and engage with the driving bevel gears 58a and 58b. The output shafts 56a and 56b of the motors 50a and 50b, the drive shafts 60a and 60b, are pivotally supported to the bracket 52 through bearings (not shown).

The lower end side of the drive shaft 60a (60b) protrudes from the lower surface of the bracket 52, and for example, an engaging protrusion 64a (64b) that has a cross-section of a hexagonal waveform and is formed in a taper shape having a tapered tip is provided in the tip of the protruded lower end (refer to FIG. 2).

As shown in FIGS. 2 and 3, the pulley box 32 includes a cavity portion 66 in which both ends are opened in the X direction, and pulleys (driven shafts) 70a and 70b and wire guide portions 72a and 72b that are accommodated in the cavity portion 66, and the shaft 18 is fixed and supported to a hole portion that penetrates the Z1 side of the cavity portion 66. A bar code (identification information recording portion of working unit) 75 facing upward is provided at the rear (X2 side) of the pulley box 32. For example, the bar code 75 is a two-dimensional bar code, is read by a camera (reading portion) 77 that is provided at the operating unit 14 side, and is a bar code for supplying the identification information such as the kind of the working unit 16 to the console 29.

The pulleys 70a and 70b have the same axis as the drive shafts 60a and 60b, and engaging recesses 74a and 74b that can engage with the engaging protrusions 64a and 64b of the drive shafts 60a and 60b side are provided at the upper end side of the pulleys. The engaging protrusions 64a and 64b can engage with (fit to) the engaging recesses 74a and 74b and for example, includes a concave portion that has a cross-section of a hexagonal waveform and a taper shape having a tapered inner portion (refer to FIG. 2).

Accordingly, when the operating unit 14 and the working unit 16 are mounted, the engaging protrusion 64a (64b) of the drive mechanism 30 side and the engaging recess 74a (74b) of the pulley box 32 side engage with each other, and therefore, the rotation driving force from the drive shaft 60a (60b) can be transmitted to the pulley 70a (70b). For example, an attachment and detachment detection sensor (not shown) that detects the attachment and detachment of the operating unit 14 and the working unit 16, a phase detection sensor (not shown) that detects a phase of the drive shaft 60a may be provided at the operating unit 14, and the engagement structure of the engaging protrusion 64a or the engaging recess 74a may have another structure.

As shown in FIGS. 2 and 3, the wire guide portion 72a (72b) is disposed at the Z1 side of the pulley 70a (70b), an interval between the wire guide portions is set so as to be narrow, and the wire guide portion have a function that guides a wire (power transmission member) 80a (80b) which is wound among a gear 78, a gear 79, and the like (refer to FIG. 4) of the pulley 70a (70b) and the tip operating unit 12 and relatively smoothly introduces the wire into the shaft 18. The wire guide portions 72a and 72b are used, and therefore, the shaft 18 can be sufficiently thin without depending on diameters of the motors 50a and 50b or an axial distance between the pulleys 70a and 70b, and for example, the shaft can be set to an outer diameter of approximately 5 mm to 10 mm that is suitable to be inserted to the trocar 20.

In addition, two rods 82a and 82b that is formed in a rod shape or line shape and is a power transmission member penetrate in the Z direction so as to be lined up in the Y direction in the cavity portion 66 that configures the pulley box 32. For example, the rods 82a and 82b are a stainless pipe or a solid rod that is sufficient strong and thin, penetrate the cavity portion 66 and extend to the inner portion of the shaft 18, and are wound around the gear 78 in the tip operating unit 12 via a wire (not shown) or the like (refer to FIG. 4). In addition, in the Z2 direction, the rods penetrate the pulley box 32 and extend to the trigger lever support portion 33 and are connected to the trigger lever 36 via a wire (not shown) or the like (refer to FIG. 3).

As shown in FIGS. 2 and 3, a pair of pinholes 84 and 84 that is symmetrical based on the Z direction is formed at the Z2 side of the pulley box 32. A pair of guide pins 86 and 86 that protrudes in the Y1 direction from the bottom surface of the bracket 52 are inserted to each of the pinholes 84 and 84 at the time of the mounting of the working unit 16 and the operating unit 14, and therefore, the operating unit 14 and the working unit 16 are positioned and mounted so as to have high stiffness.

In the working unit 16, each of wires 80a and 80b is reciprocated between the pulleys 70a and 70b side and the tip operating unit 12 side, and therefore, four extended wires 80a and 80b and two rods 82a and 82b are inserted into the hollow space of the shaft 18. For example, all power transmission mechanisms may be configured by only wires instead of the rods. Each of wires 80a and 80b may be the same kind as or different kind from each other, may be the same diameter as or different diameter from each other, and is configured of a bendable wire having flexibility. In the wires 80a and 80b, a linear portion in which the flexibility is not needed in a portion passing through the inner portion of the shaft 18 is surrounded by a reinforcement rod having high stiffness (not shown) and may be refined.

Accordingly, in the manipulator 11, if the composite input unit 24 is operated, the motors 50a and 50b are driven and controlled under the control of the console 29, and therefore, the wires 80a and 80b are driven so as to reciprocate via the pulleys 70a and 70b from the drive shafts 60a and 60b, and the rotation operation (operation in the roll direction) having the roll axis Or as a center and the swing operation (operation in the yaw direction or operation in the pitch direction) having the yaw axis Oy as a center are applied to the tip operating unit 12 (refer to FIG. 4). In addition, the trigger lever 36 is operated to be rotated, therefore, the rods 82a and 82b are mechanically driven so as to reciprocate, and an opening and closing operation is applied to the scissors 48 of the tip operating unit 12.

The pulleys 70a and 70b (motors 50a and 50b) and the trigger lever 36 apply the driving force to the wires 80a and 80b and the rods 82a and 82b which are a power transmission member and function as a drive mechanism portion that operates the tip operating unit 12. More specifically, the pulleys 70a and 70b (motors 50a and 50b) apply the driving force to the wires 80a and 80b and function as an electric mechanism portion that applies the operation in the roll direction and yaw direction to the tip operating unit 12. In addition, the trigger lever 36 applies the driving force to the rods 82a and 82b and functions a manual mechanism portion that applies the opening and closing operation of the scissors 48 to the tip operating unit 12.

Figure 6:
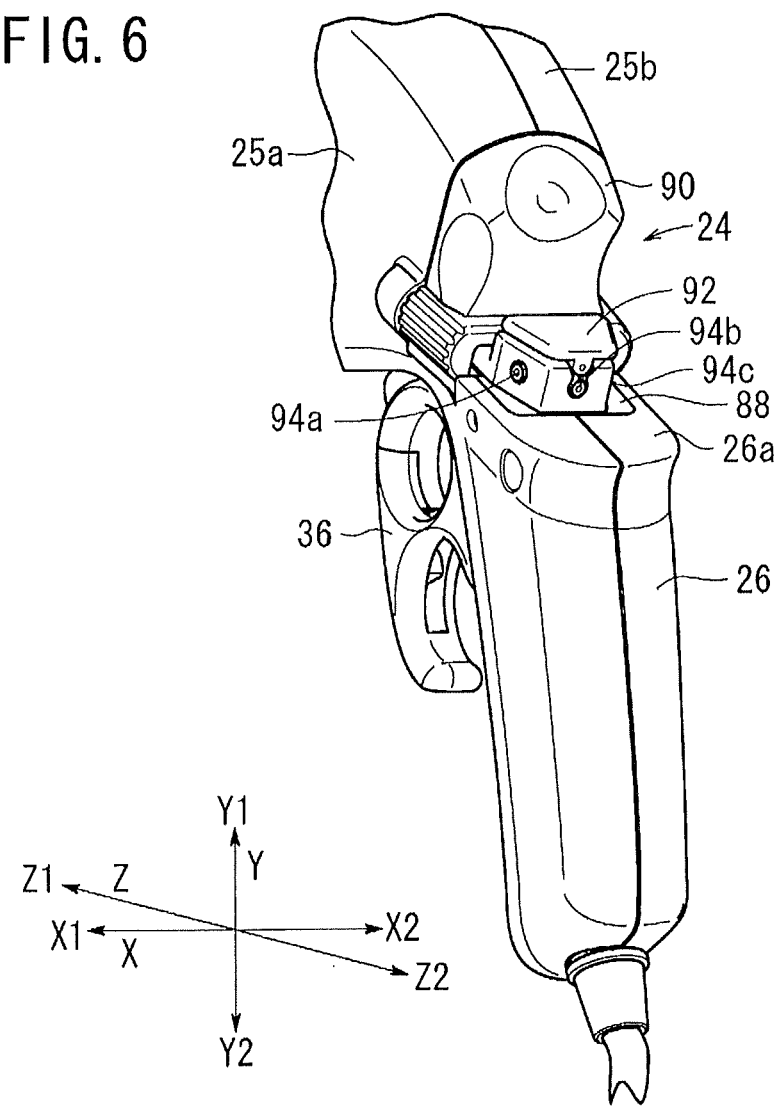
FIG. 6 is a perspective view of the manipulator in which a portion of the composite input unit and the peripheral portion of the manipulator are omitted.

As shown in FIG. 6, the composite input unit 24 that electrically drives the tip operating unit 12 has a structure that is symmetrical in the X1 and X2 directions with the Z axis (Y axis) as a center and is a composite input unit that applies a rotation command in the roll direction (axis rotation direction) and the yaw direction (left and right directions) with respect to the tip operating unit 12.

The composite input unit 24 is supported by a sensor holder 88 that is disposed on the inclined plane 26a, and includes a rotation operating unit 90 of the Z1 side (Y1 side) of the inclined plane 26a, a tilting operating unit 92 that is provided at the Z2 side (Y2 side), and three switch operators 94a to 94c that are disposed on the surface of the lower portion side of the tilting operating unit 92 respectively. The operation amount in the input to the rotation operating unit 90 is detected by a switch substrate (not shown) that is provided in the sensor holder 88, and the motors 50a and 50b are appropriately driven and controlled under the control of the console 29.

The console 29 is a controller (control portion) that synthetically controls the manipulator system 10. Moreover, a portion of a function of the console 29 may be loaded to the operating unit 14. As shown in FIGS. 1 and 5, the console 29 includes two connectors 100 and 102 and can independently and simultaneously control two manipulators 11.

The console 29 may be connected to a host computer (not shown) which is use history management means via communication means such as a LAN. The host computer records a use history table at recording means of the inner portion, sends and receives a use history data according to an individual number (identification number) for the console 29 or a plurality of consoles 29 connected through the LAN, and manages the use history data. The host computer is not limited to a configuration independent of the console 29 and the functions of the host computer may be provided in the inner portion of the console 29.

Figure 7:
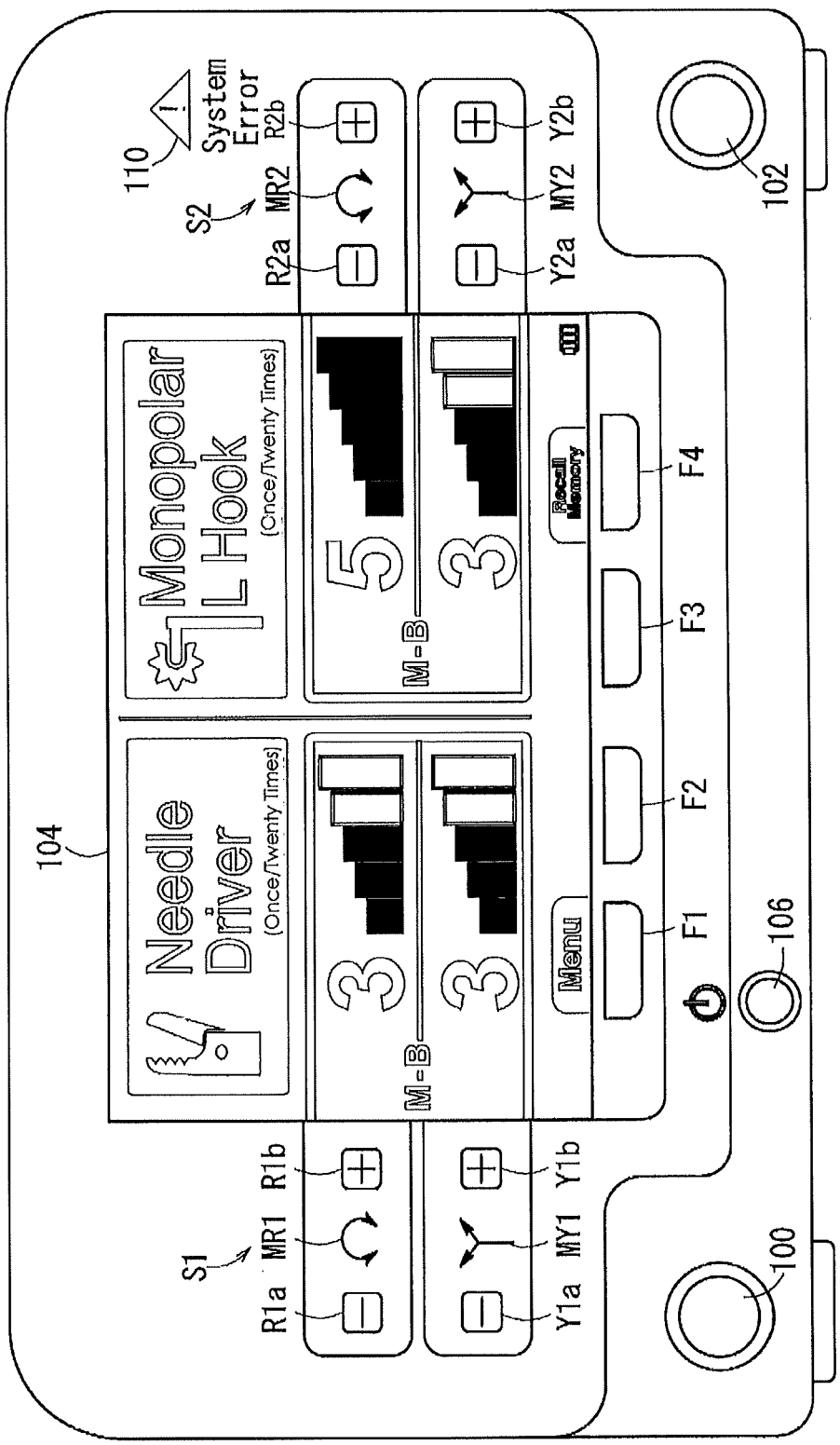
FIG. 7 is a front view of a console in a state where a speed display screen is displayed on a display.

As shown in FIG. 7, the first connector 100 and the second connector 102 are provided so as to be separated from each other in the left and right at a front panel of the console 29, and the first setting switch S1 and the second setting switch S2 are disposed while interposing a center display 104 so as to correspond to two manipulators 11 connected to each of connectors. The first connector 100 and the first setting switch S1 become a first channel corresponding to one side of the manipulator 11, and the second connector 102 and the second setting switch S2 become a second channel corresponding to the other side of the manipulator 11. The number of the channels may be increased according to the use condition or configuration.

In addition, in the front panel of the console 29, a plurality of (four in the present embodiment) function switches F1, F2, F3, and F4 that are provided along the lower side of the display 104, a power supply switch 106 that turns on and off the power of the console 29, and an error display portion 110 that displays various system errors such as a connection error between the operating unit 14 and the working unit 16 in the manipulator 11 with a flickering light (with a blinking light) are provided.

As shown in FIG. 7, the first setting switch S1 performs a speed change of the tip operating unit 12 of the manipulator 11 that is connected to the first connector 100 and includes a pair of roll speed change buttons R1a and R1b that is provided in the left and right at the upper stage and a pair of yaw speed change buttons Y1a and Y1b that is provided in the left and right at the lower stage. The roll speed change buttons R1a and R1b are a setting input unit for decreasing (R1a) and increasing (R1b) the speed of the rotation operation in the roll axis Or direction of the tip operating unit 12, and a mark MR1 specifies that the roll speed change buttons R1a and R1b are the switches changing the speed of the roll operation is provided between the roll speed change buttons. The yaw speed change buttons Y1a and Y1b are a setting input unit for decreasing (Y1a) and increasing (Y1b) the speed of the swing operation in the yaw axis Oy direction of the tip operating unit 12, and a mark MY1 specifies that the yaw speed change buttons Y1a and Y1b are the switches changing the speed of the yaw operation is provided between the yaw speed change buttons.

Except that the second setting switch S2 is an input unit that changes the speed of the rotation operation in the roll axis Or direction and the speed of the swing operation in the yaw axis Oy direction of the tip operating unit 12 of the manipulator 11 connected to the second connector 102, the second setting switch is approximately similar to the first setting switch S1. The second setting switch S2 includes a pair of roll speed change buttons R2a and R2b that is provided in the left and right at the upper stage, a pair of yaw speed change buttons Y1a and Y1b that is provided in the left and right at the lower stage, a mark MR2, and a mark MY2.

According to the first setting switch S1 and the second setting switch S2, in the manipulator system 10, for example, the operating speed of the roll-axis operation and yaw-axis operation of each working unit 16 is set and changed to five levels such as "5 (fast)", "4 (slightly fast)", "3 (reference speed)", "2 (slightly slow), "1 (slow)", and can be appropriately adjusted according to preference or manipulation of a user. For example, if the roll speed change buttons R1a and R1b and the yaw speed change buttons Y1a and Y1b of the first setting switch S1 are operated, since the operating speed of the tip operating unit 12 is set in the manipulator 11 that is connected to the first connector 100 corresponding thereto, an operation management unit 118 controls the drive of the motors 50a and 50b at the set operating speed, and therefore, the operating speed of the tip operating unit 12 is controlled to have a desired speed.

For example, in the display 104, as shown in FIG. 7, the set speed of the roll-axis operation and the yaw-axis operation through the first setting switch S1 and the second setting switch S2 can be displayed by the disposition corresponding to each of setting switches S1 and S2. The display 104 can display the information of each of manipulators 11 that are connected to the first connector 100 and the second connector 102 in the left and right of the screen respectively, the kind of the working unit 16 (tip operating unit 12) is displayed in a graphic form and a name in the upper stage, a usage count of the working unit is displayed in figures, the operating speed corresponding to the set values at each of setting switches S1 and S2 is displayed in figures and a graphic form in the middle stage, and current functions of the function switches F1 to F4 disposed along the lower side of the display 104 can be displayed in the lower stage respectively.

Since two manipulators can be individually and simultaneously driven and controlled in the console 29, for example, if the display of the first setting switch S1 configuring the first channel and the display of the left half of the middle stage of the display 104 that shows the operating speed of the manipulator 11 corresponding to the first setting switch in figures and graphs are configured so as to be surrounded by the same color, and the display of the second setting switch S2 and the display of the right half of the middle stage of the display 104 that shows the set values of the second setting switch are configured so as to be surrounded by the color different from the above-described color, the setting and the change of the operating speed of each of manipulators 11 can be more easily performed.

For example, the console 29 corresponds to five kinds of the tip operating units 12 (working units 16) as described above, the set speed of the roll-axis operation and the yaw axis operation of five kinds of the tip operating units 12 can be individually set and stored according to the preference of a plurality of (for example, eight) users (doctors) respectively.

Figure 8:
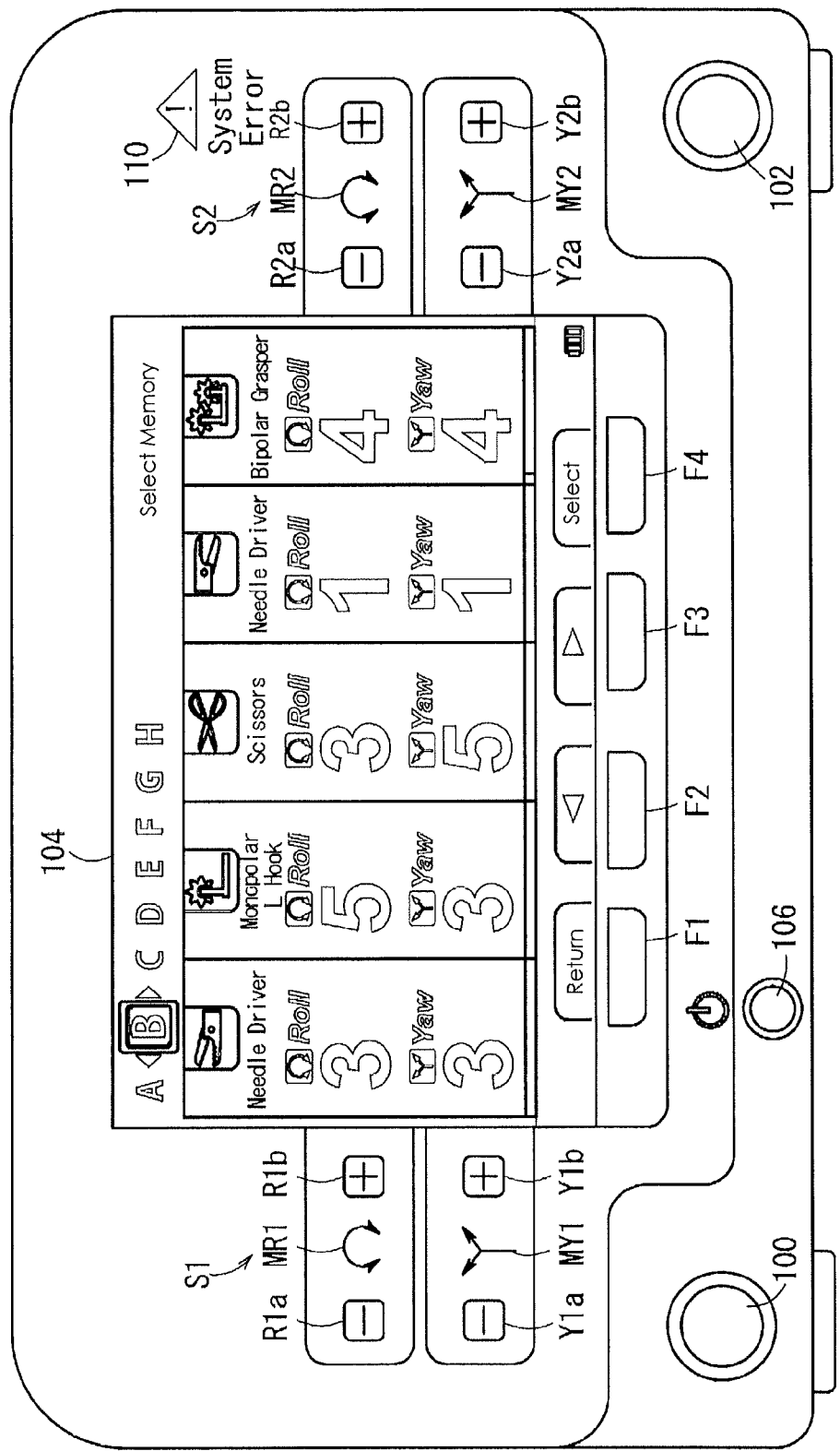
FIG. 8 is a front view of the console in a state where a memory selection screen is displayed on the display.

Thereby, as shown in FIG. 8, the display 104 can collectively display the set speed of the roll-axis operation and the yaw-axis operation that are set and stored for each kind of the tip operating unit 12. For example, the display 104 can display memories A, B, C, D, E, F, G, and H that are an individual set speed folder of every eight users, enlarge and invertedly display a current selected memory name (memory B in FIG. 8) in the upper stage, can display the kind of the working unit 16 (tip operating unit 12) in the selected memory by a graphic form and a name and display the set speed of the roll-axis operation and yaw roll-axis operation by a mark, a name, and figures in the middle stage, and can display the current function of the function switches F1 to F4 in the lower stage respectively. For example, after the screen of the set speed shown in FIG. 8 displays the information of the manipulator 11 that is connected to the first connector 100, if the set is completed, subsequently, the screen automatically displays the information of the manipulator 11 that is connected to the second connector 102. A button that selects the display of the information of the manipulator 11 connected to which of the first and second connectors 100 and 102 may be added to the function switches F1 to F4.

In addition, in FIG. 8, a case where a needle drive (Needle Driver), a monopolar L hook (Monopolar L Hook), a scissors (Scissors), a needle driver (Needle Driver), and a bipolar grasper (Bipolar Grasper) are used in turn from left as five kinds of tip operating units 12 is exemplified. In addition, in FIG. 7, a case where the needle drive (Needle Driver) is connected to the first connector 100, the monopolar L hook (Monopolar L Hook) is connected to the second connector 102, and the set information of the memory B (shown as "M-B" in FIG. 7) is displayed is exemplified.

Figure 9:
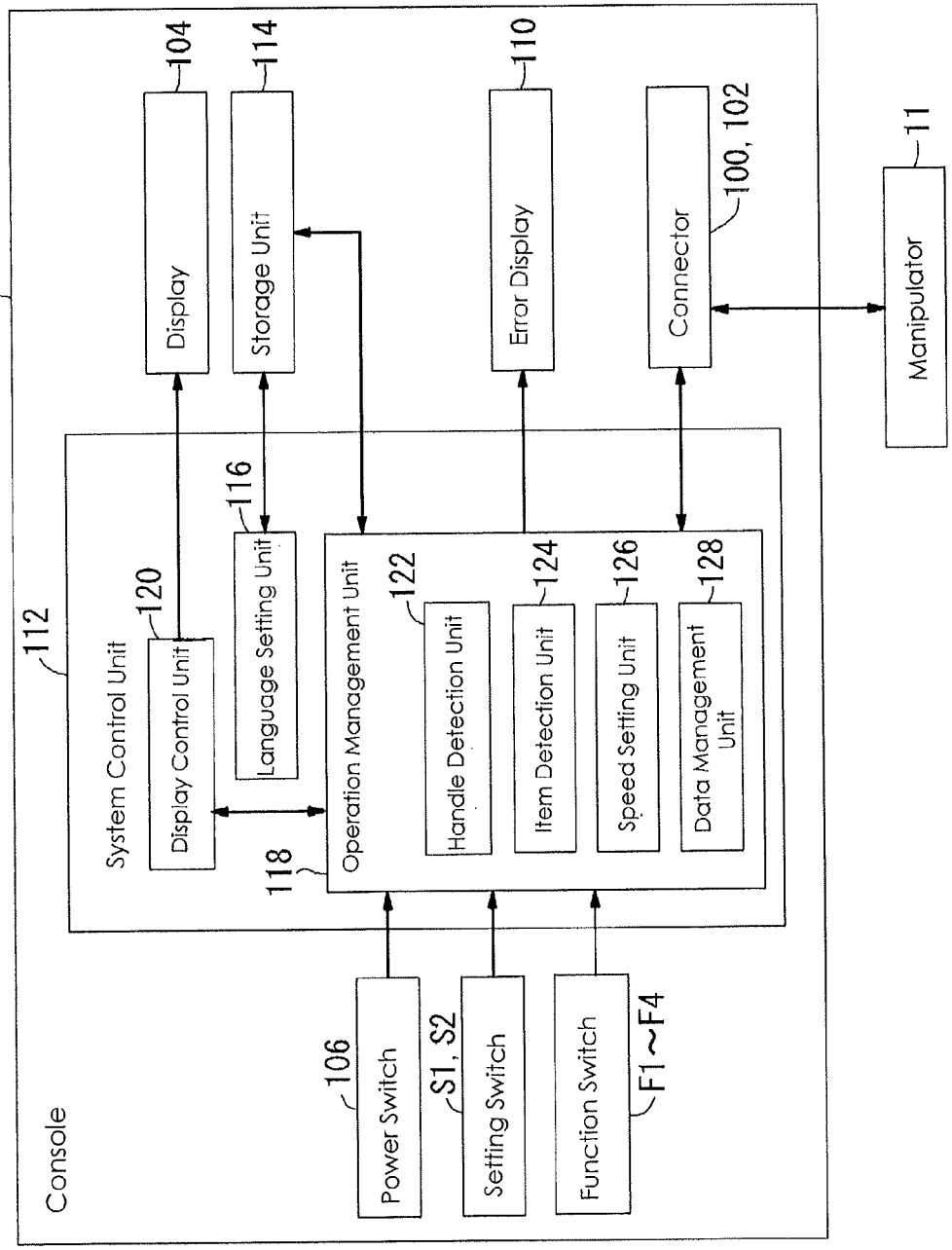
FIG. 9 is an explanatory block diagram of functions that are included in the console.

The console 29 will be described with reference to FIG. 9. FIG. 9 is an explanatory block diagram of functions that are included in the console 29.

As shown in FIG. 9, the console 29 includes the power supply switch 106, the setting switches S1 and S2, the function switches F1 to F4, the display 104, the error display portion 110, and the connectors 100 and 102, and further includes a system control unit 112 and a storage unit 114.

The system control unit 112 is a synthetic control unit of the console 29 that includes a language setting unit 116, an operation management unit 118, and a display control unit 120.

For example, the language setting unit 116 sets a language (for example, Japanese, English, Chinese, French, and Spanish) that is displayed and used in the console 29 according to an initial setting at the time of the initial starting or an arbitrary set change, the set is stored in the storage unit 114, thereafter, the display on the display 104 is performed according to the set language (or the changed language), and the operation of the console 29 can be performed.

The operation management unit 118 includes a handle detection unit 122 that detects the operating unit 14 which is a handle connected to the connectors 100 and 102, an item detection unit 124 that detects the working unit 16 which is an item mounted to the handle (operating unit 14), a speed setting unit 126 that sets the speed of the roll-axis operation and yaw-axis operation of the tip operating unit 12, and a data management unit 128 that manages various data such as the identification information (individual number, or kind of tip operating unit 12) of the working unit 16 that is read by photographing the set speed information or the bar code 75 (refer to FIG. 2) of each tip operating unit 12 with a camera 77 while using the storage unit 114.

The display control unit 120 receives the supply of various information from the operation management unit 118, performs arithmetic processing of the information, and displays the processed information on the display 104. In addition, the display control unit also performs a display processing for the function information that is divided in the function switches F1 to F4.

Figure 10:
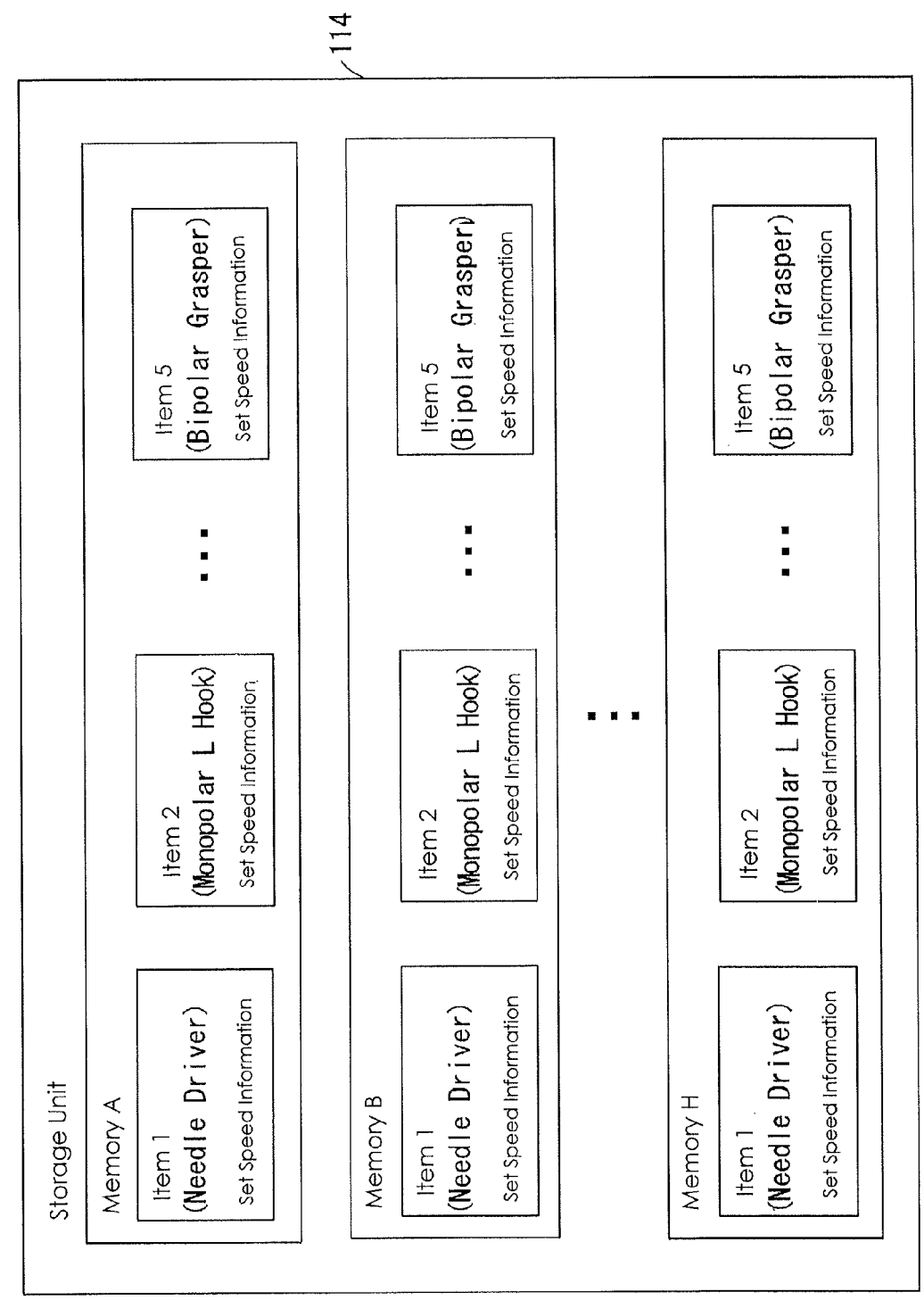
FIG. 10 is an explanatory diagram showing an example of information that is registered in a storage unit.

The storage unit 114 is a memory (for example, a RAM) that stores the set language at the language setting unit 116, the set speed information of the roll-axis operation and yaw-axis operation that is set and stored for each kind of the tip operating unit 12. As shown in FIG. 10, in the storage unit 114, the set speed information of the roll-axis operation and the yaw-axis operation can be registered at eight groups A to H of the memory, and the set speed information of five kinds of items 1 to 5 for each set can be registered in each of the eight groups.

A method of setting the speed of the tip operating unit 12 using console 29 and the operation of the tip operating unit 12 will be disclosed.

First, a desired calling out procedure of the memories A to H and a use preparation procedure of the manipulator system 10 will be disclosed.

Figure 11A:
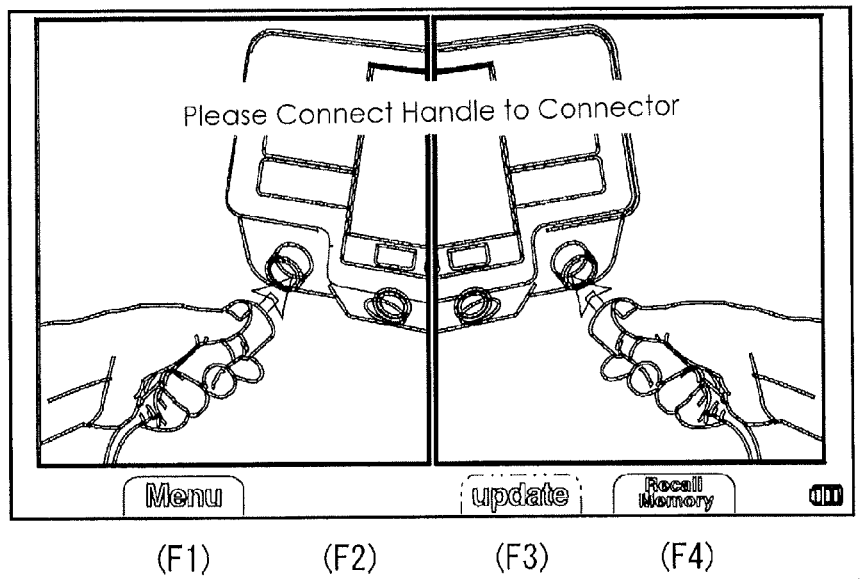
FIG. 11A is an explanatory diagram showing an example of an image of prompting a connection of the operating unit to a connector.
Figure 11B:
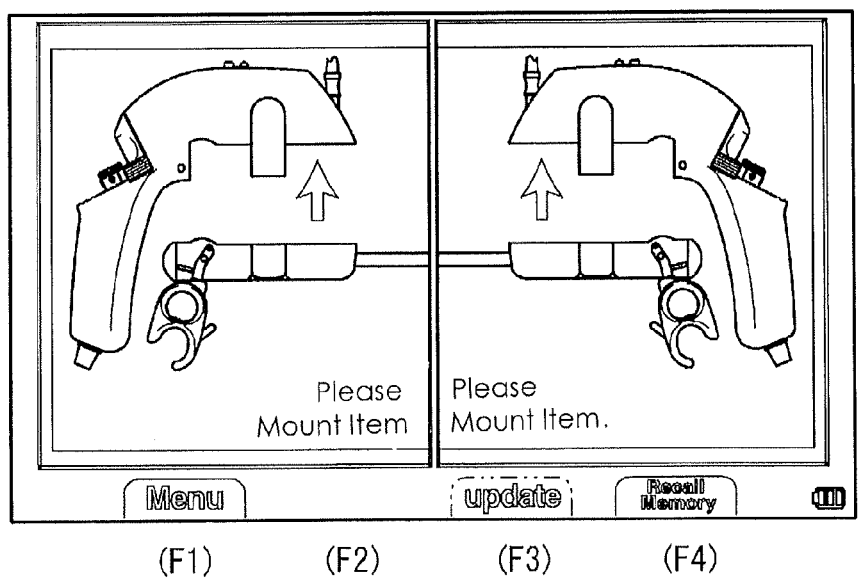
FIG. 11B is an explanatory diagram showing an example of an image of prompting a mounting of a working unit to the operating unit.

If the power supply switch 106 is turned on and the console 29 starts, under the control of the operation management unit 118 and the display control unit 120, as shown in FIG. 11A, an image that prompts the connection of the operating unit 14, which is the handle, to the connectors 100 and 102 is displayed on the display 104. Subsequently, if the operating unit 14 is connected, the connection is detected by the handle detection unit 122. In addition, as shown in FIG. 11B, since an image that prompts the mounting of the working unit 16, which is an item, to the operating unit 14, if a desired working unit 16 is mounted to the operating unit 14, the mounting is detected by the item detection unit 124. For example, where the operating unit 14 is connected to only the first connector 100, the left half of the screen displays the image that prompts the mounting of the item, and the right half of the screen displays the image that prompts the mounting of the handle to the second connector 102.

Figure 12A:
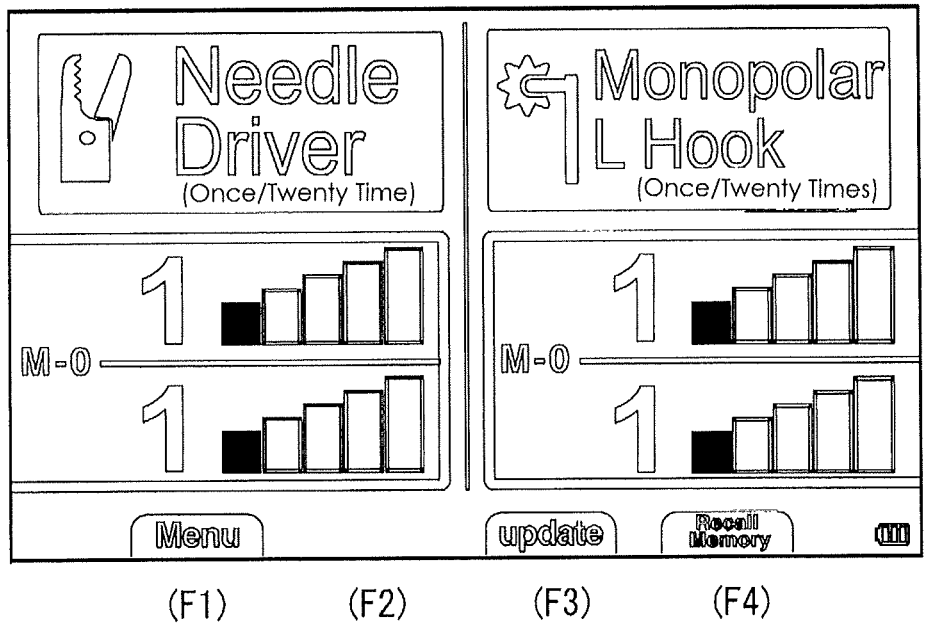
FIG. 12A is an explanatory diagram showing an example of an initial speed display screen.
Figure 12B:
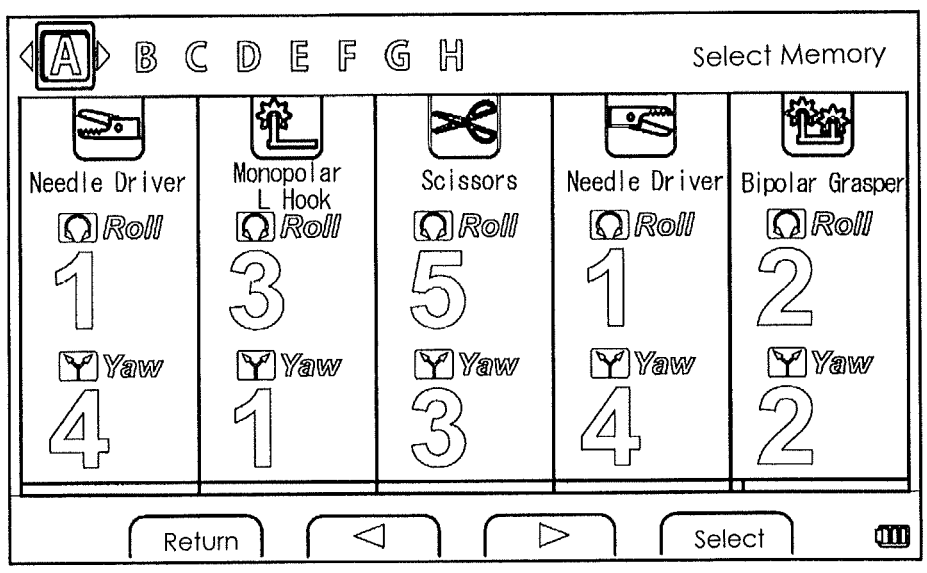
FIG. 12B is an explanatory diagram showing an example of a memory selection screen.

If the manipulator 11 is connected to each of connectors 100 and 102, as shown in FIG. 12A, an initial speed display screen (M-0), which is a TOP screen in a state where the memories A to H are not selected, is displayed on the display 104. In addition, the kind of the manipulator 11 (tip operating unit 12) that is connected to each of connectors 100 and 102 is displayed on the initial speed display screen based on the identification information that is achieved through the bar code 75 and the camera 77. Thereby, the user selects a "Recall Memory" of the function switch F4, and therefore, as shown in FIG. 12B, the user can proceed on the selection screen of the registered memories A to H. In the memory selection screen, the function switches F1 to F4 are selected and operated according to the screen instruction, and for example, as shown in FIG. 8, a desired memory B can be selected.

Therefore, under the management of the data management unit 128, with respect to the working unit 16 that is currently connected to each of connectors 100 and 102, the set speed information that is registered in the memory B according to the kind of the tip operating unit 12 is read from the storage unit 114, the read information is displayed as shown in FIG. 7, and the use preparation of the manipulator system 10 is completed.

Next, a method of changing the set speed of the tip operating unit 12 and a method of registering it during use will be disclosed.

For example, while surgery is performed at the set speed (M-B) shown in the screen (TOP screen, speed display screen) at the time of use of the console 29 shown in FIG. 7 or the set speed (M-0) shown in the initial speed display screen shown in FIG. 12A, when the operating speed of the tip operating unit 12 is to be changed, the first setting switch S1 (roll speed change buttons R1$a$ and R1$b$ and yaw speed change buttons Y1$a$ and Y1$b$) or the second setting switch S2 (roll speed change buttons R2$a$ and R2$b$ and yaw speed change buttons Y2$a$ and Y2$b$) are appropriately operated. Thereby, the operating speed corresponding to the operation is changed and the display of figures and the graphic form in FIG. 7 is also simultaneously changed. Therefore, the user can rather easily and correctly change the operating speed while viewing the display 104, and the operating speed can flexibly correspond to an optimal operating speed according to the manipulation. In addition, since the first and second setting switches S1 and S2 are disposed so as to correspond to each of the first and second connectors 100 and 102 in the left and right, the user can more intuitively and correctly perform the speed change of the desired manipulator 11 between two manipulators 11.

Figure 13A:
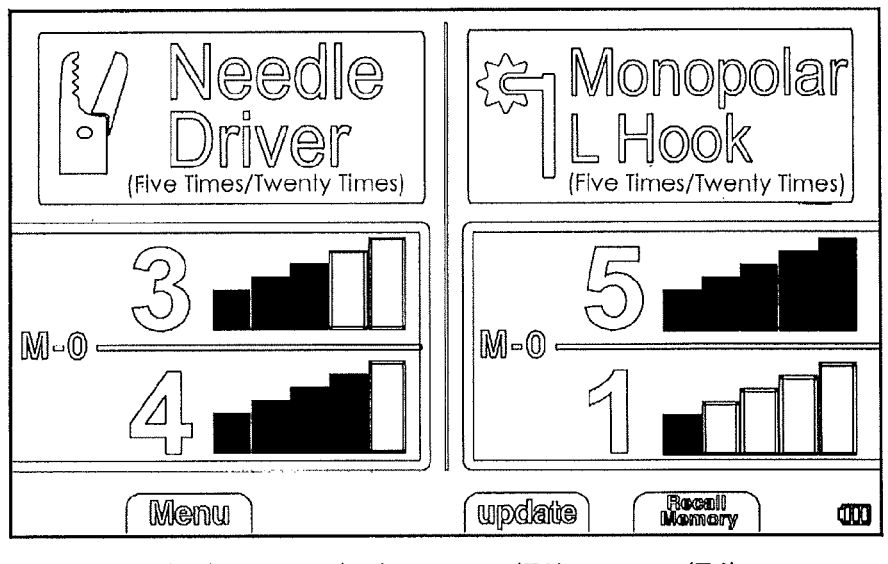
FIG. 13A is an explanatory diagram showing an example of the speed display screen when the speed change of the tip operating unit is performed during use.

In this way, when the operating speed is changed during use, as shown in FIG. 13A, the display at the middle stage of the display 104 becomes the "M-0" similar to the initial speed display, and "Update" is displayed on the function switch F3. Therefore, the function switch F3 is selected and operated, the set speed after the change can be registered at the desired memory among the memories A to H. Of course, the set speed after the change may be registered to be overwritten on the memory that is called out at the start of the use, may be registered to be overwritten on another memory, or may be registered on an empty memory on which the speed information is not registered.

Figure 13B:
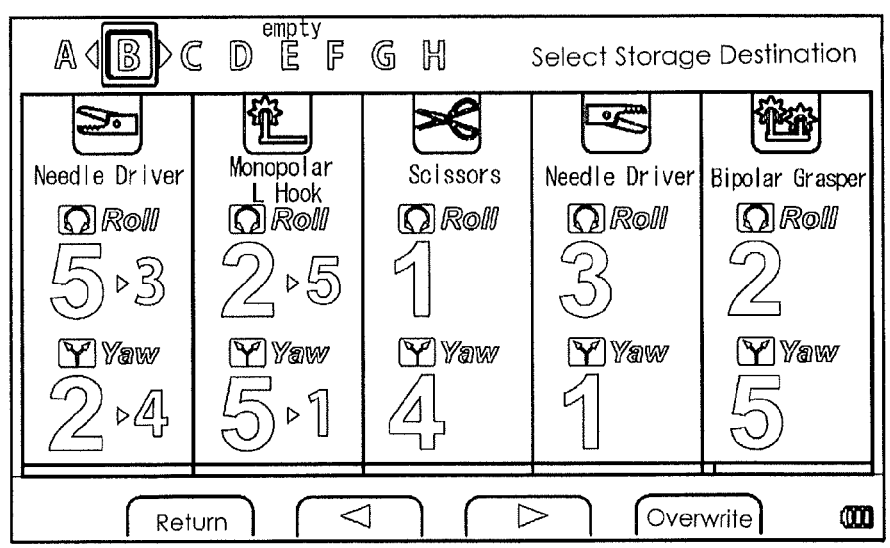
FIG. 13B is an explanatory diagram showing an example of a registration destination memory selection screen that is displayed followed by the screen displayed in FIG. 13A.

For example, during the use of the manipulator system 10 with the set of the memory B, when in the speed before the change (that is, the speed that is registered on the memory B in advance), the operating speed of the roll axis is "5 (the fastest)" and the operating speed of the yaw axis is "2 (slightly slow)" in the needle driver (Needle Driver) of the item 1 and, as shown in FIG. 13A, in the speed after the set is changed during the use, the operating speed of the roll axis is "3 (reference speed)" and the operating speed of the yaw axis is "4 (slightly fast)", as shown in FIG. 13B, the speed after the change, which has a changed color and slightly smaller font than the numeral of the speed before the change while interposing an arrow traversely at the right side of the numeral indicating the speed before the change, is displayed in parallel.

Thereby, as shown in FIG. 13B, the user can view and compare the set speed information before the change and the set speed information after the change on the screen, select and operate the function switch F4 to the "overwriting" function is added, and therefore, can rather easily change and register the information to the original memory B. When the user is to overwrite the set speed information after the change on another memory A, the user appropriately operates the function switches F2 and F3, displays the information of another memory, and may perform the overwriting operation while viewing and comparing the speed information before the change and the speed information after the change on the screen. In addition, in FIG. 13B, since the set speed information is not registered in the memory E, a display of "empty" is performed on the upper portion of the display of "E", and therefore, it is specified that the memory E is an empty memory.

The change and registration is processed through the speed setting unit 126 of the operation management unit 118, and the speed display screen (TOP screen) as shown in FIG. 7 is automatically displayed on the display 104 again through the operation management unit 118 and the display control unit 120 after the registration is completed. Therefore, the user relatively smoothly proceeds to the next manipulation or ends the manipulation.

In addition, the storage unit 114 of the console 29 has a specification in which the same kind of single item can be only registered in one of the memories A to H.

Figure 14A:
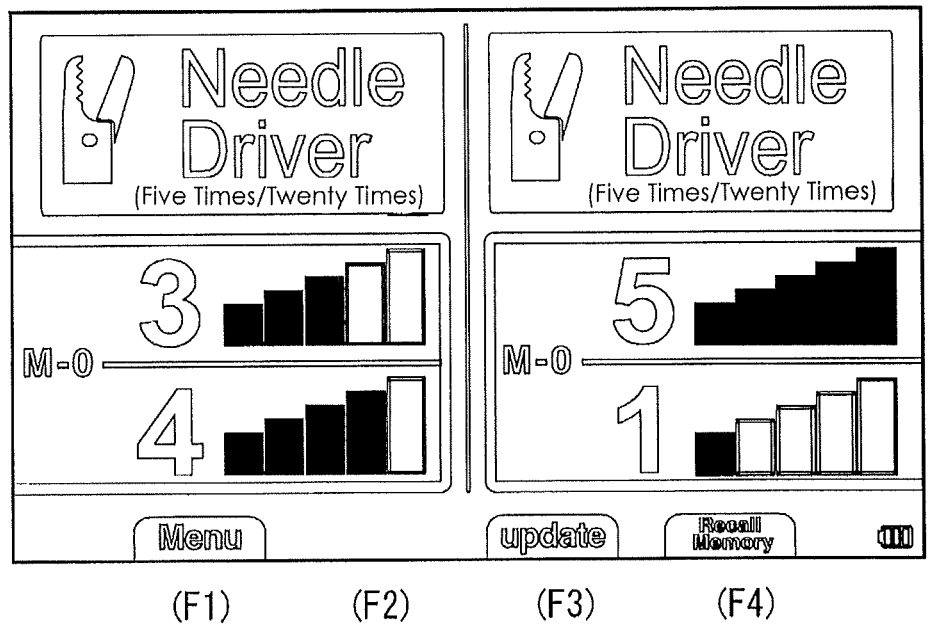
FIG. 14A is an explanatory diagram showing an example of the speed display screen in a state where the manipulator having the same kind of tip operating units is connected to each connector.
Figure 14B:
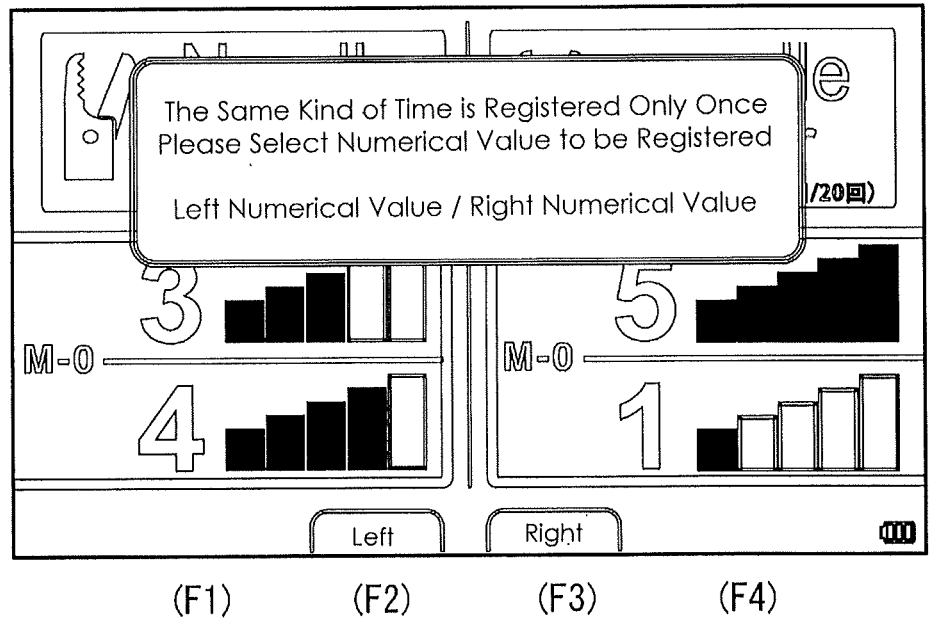
FIG. 14B is an explanatory diagram showing an example of a selection screen of the manipulator that registers a setting speed after the change after the manipulator having the same kind of tip operating units is used in a state of being connected to each connector.

Therefore, as shown in FIG. 14A, when the working unit 16 having the same kind of tip operating unit 12 is connected to each of connectors 100 and 102 and used (In FIG. 14A, two manipulators 11 are the "Needle Driver") and the operating speed is changed during the use, as shown in FIG. 14B, whether or not to register the left set value or the right set value is displayed on the selection screen, and therefore, a desired set value can be changed and registered as the set after the change. In FIG. 14B, either the function switch F2 ("right") or the function switch F3 ("left") is selected and operated, and therefore, the screen for registering the selected set value (approximately similar to the screen of the change and registration of FIG. 13B) is displayed.

In the console 29, the information of each of memories A to H may be changed before the manipulation starting such as before the connection of the manipulator 11 or may be newly registered. In this case, since the registration operation is prompted according to the function switches F1 to F4 and the screen display, the user rather easily can perform the set registration according to the similar display to the display shown in FIG. 13B. Removal of the registration information of unnecessary memories A to H can be also performed.

In addition, after the surgery, when the set speed information of the manipulator 11 in the last use is to be registered again after the manipulator 11 is removed from the connectors 100 and 102 or the working unit 16 is removed from the operating unit 14, as shown by a two-dot chain line in FIGS. 11A and 11B, "Update" is displayed on the function switch F3. Thereby, the function switch F3 is selected and operated, and the set speed information in the last use that is temporarily stored in the storage unit 114 is displayed on the display 104 through the similar screen to the change and registration screen as shown in FIG. 13B. Therefore, the change and registration can be rather easily performed through the similar procedure to that of the general set and change.

As described above, in the manipulator system 10, in the tip operating unit in which the rotation operation in the roll direction and the swing operation in the yaw direction (or pitch direction) can be performed, the speed setting unit 126 in which the operating speed can be changed is included in the console 29. In addition, since the speed setting unit 126 performs the speed set according to the selection operation of the first setting switch S1 and the second setting switch S2, the setting switches S1 and S2 may be included in the speed setting unit. Therefore, according to the individual differences of the user (doctor) handling the manipulator 11 or the kind of the tip operating unit 12 (scissors or needle driver), the operating speed of the rotation operation in the roll direction and the swing operation in the yaw direction can be optimally set and changed, and high operability can be achieved.

In addition, at least one (for example, only in the roll direction) of the changes of the operating speed in the roll direction or yaw direction (or pitch direction) may be performed, in a case of considering securing of high operability, it is preferable that the settings of both can be individually changed. In addition, in the embodiment, the manipulator system 10 that includes the console 29, which simultaneously controls two manipulators 11, is exemplified. Of course, the system may have only a single manipulator 11, or the system may have 3 or more manipulators 11.

Figure 15:
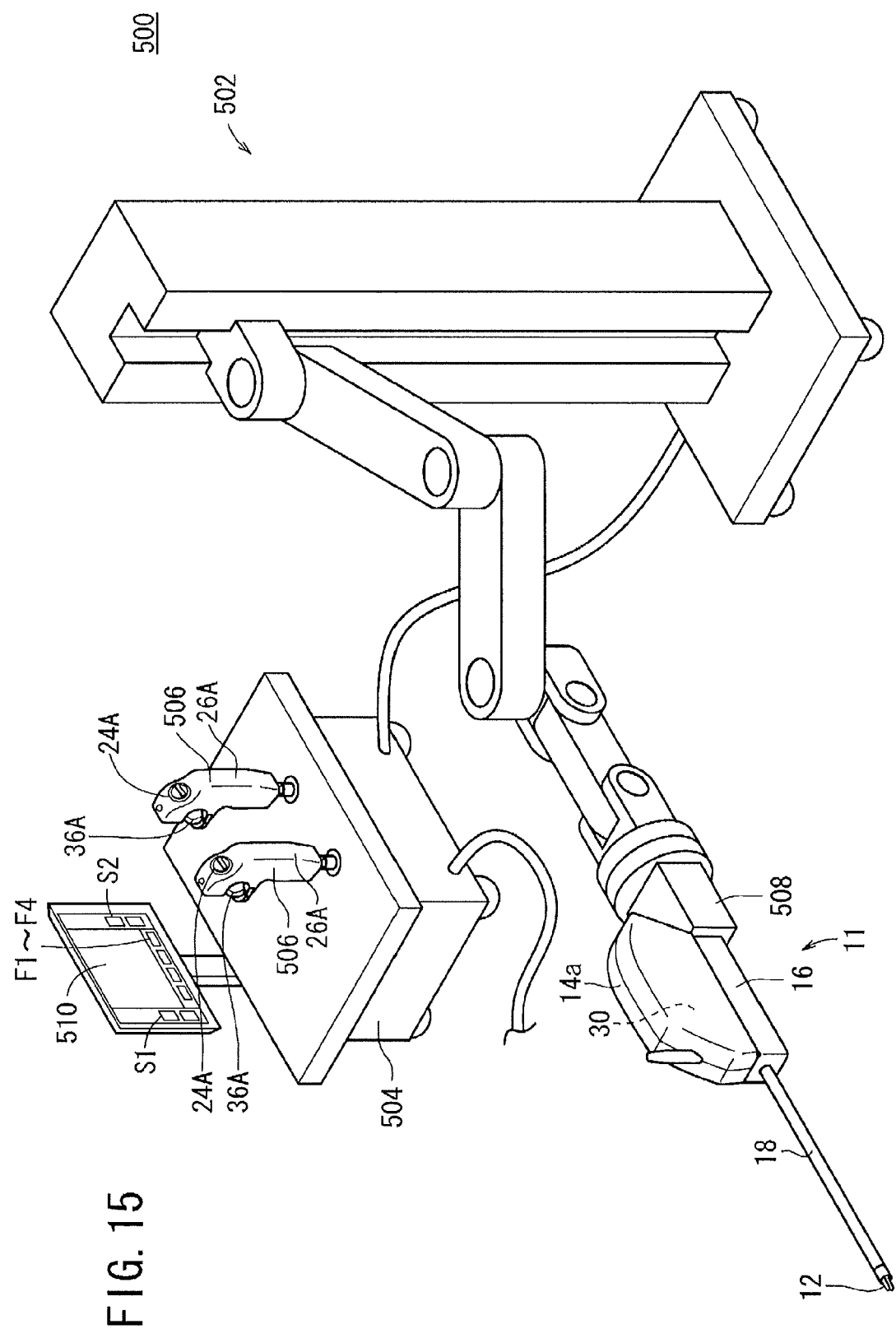
FIG. 15 is a schematic perspective view of a robot system for surgery.

For example, the present invention can be applied to a robot system for surgery 500 shown in FIG. 15.

The robot system for surgery 500 includes a multiple joint type robot arm 502 and a console (controller) 504 that controls the robot arm, and a mechanism similar to the above-described manipulator 11 is provided on the tip of the robot arm 502. A base portion 14a that accommodates the drive mechanism 30 in the inner portion instead of the operating unit 14 is fixed to the tip 508 of the robot arm 502, and the working unit 16 in which the tip operating unit 12 is provided is mounted so as to be attached to and detached from the base portion 14a.

The robot arm 502 may be any means for moving the working unit 16, is not limited to a stationary type, and for example may be autonomously mobile type. If the robot arm 502 includes 6 or more joints (rotation shafts or slide shafts) that are independent to each other, it is preferable since the position and the direction of the working unit 16 can be arbitrarily set. The base portion 14a configuring the manipulator 11 of the tip is integrated with the tip 508 of the robot arm 502.

In the console 504, two joy sticks 506 and a monitor 510 which are an operation command unit are provided. The console 504 may adopt a configuration such as a table type or control panel type. The robot arm 502 is operated under the operation of the console 504, and an automatic operation through a program, an operation according to the joy sticks 506 provided in the console 504, or the composite operations thereof may be configured. The console 504 includes the functions of the console 29.

In this case, functions similar to the display 104 (refer to FIG. 7) are provided in the monitor 510, those similar to the first and second setting switches S1 and S2 or the function switches F1 to F4 are installed at the periphery of the monitor 510, and similar to the console 29, the system control unit 112 and the storage unit 114 are mounted to the console 504. In addition, the base portion 14a and the joy sticks 506 act as the functions similar to the operating unit (main body portion) 14 (refer to FIG. 1).

According to two joysticks 506, two robot arms 502 can be individually operated. In addition, in FIG. 15, a single robot arm 502 is shown. However, similar to the manipulator system 10, two robot arms may be provided. Two joy sticks 506 are provided at a position where an operation is rather easily performed with both hands. The joy sticks 506 may perform up and down operations, left and right operations, a twist operation, and a tilting operation, and the robot arm 502 can move according to the operation. The joy sticks 506 may be a master arm.

A grip handle 26A, a trigger lever 36A that is operated to be pulled and pushed, and a composite input unit 24A that is operated to be rotated and be tilted are provided in the joy sticks 506. The trigger lever 36A is a substitute for the trigger lever 36, the trigger lever 36A is operated, and therefore, two rods 82a and 82b (refer to FIG. 3 and not shown in FIG. 15) can be driven to advance and retreat through a motor (not shown) (actuator that drives in conjunction with the input unit operated by hands). The composite input unit 24A is a substitute for the composite input unit 24, the composite input unit 24A is operated, thereby, the drive mechanism 30 is controlled by the console 504 according to the content of the operation, and the roll operation, the tilting operation, or the composite operation thereof of the tip operating unit 12 is performed. At this time, the first setting switch S1 provided in the console 504 is operated, and therefore, similar to the manipulator system 10, the changing and setting registration of the operating speed of the tip operating unit 12 can be performed.

Communication means between the robot arm 502 and the console 504 may be made by wire, wireless, networks, or a combination thereof. The information on an image is displayed on the monitor 510 through a flexible mirror.

The detailed description above discloses a medical manipulator, but the disclosed and illustrated embodiments are not intended to restrict the scope of the present invention as defined in the accompanying claims. Various changes, modifications and equivalents could be effected by one skilled in the art without departing from the spirit and scope of the invention as defined in the accompanying claims. It is expressly intended that all such changes, modifications and equivalents, which fall within the scope of the claims be embraced by the claims.

What is claimed is:

1. A medical manipulator system comprising:
 a plurality of medical manipulators, each of said medical manipulators including:
  a main body portion that includes drive shafts which are rotated by actuators and an input unit which drives the actuators; and
  a working unit that includes driven shafts which are rotatably driven by the main body drive shafts, a tip operating unit which is operated by the rotation of the driven shafts, and a shaft which is provided at a tip of the tip operating unit;
 a controller including at least two connectors, each of which is configured to be connected to one of the plurality of medical manipulators, wherein the controller independently and simultaneously controls the actuators of the medical manipulators based on an input operation to the input unit;
 wherein the actuators are driven based on the input operation to the input unit, and wherein the tip operating unit performs at least a rotation operation along an axial direction or a swing operation that crosses the axial direction;
 wherein the controller changes driving speeds of the actuators, and includes a speed setting unit which sets an operating speed of a rotation operation or a swing operation for each of the medical manipulators, and which changes the operating speed of the rotation operation or the swing operation of the tip operating unit according to a stored preference of one of a plurality of predetermined users; and
 wherein the speed setting unit simultaneously displays, based on a user-selected memory folder, the operating speed of the rotation operation or the swing operation for the tip operating unit for each medical manipulator connected to the at least two connectors and displays the set driving speed of the actuators before a change of speed and after the change of speed such that the user can view and confirm changing the set speed, and such that the speed of each medical manipulator connected to the at least two connectors can be simultaneously changed.

2. The medical manipulator system according to claim 1, wherein the tip operating unit performs the rotation operation and the swing operation, and the speed setting unit individually changes the operating speeds of the rotation operation and the swing operation, respectively.

3. The medical manipulator system according to claim 2, wherein the controller includes a storage unit that stores a set value of the operating speed of the tip operating unit through the speed setting unit, and a combination of the set values of the operating speed of the rotation operation and the swing operation are registered in a plurality of combinations in the storage unit.

4. The medical manipulator system according to claim 3, wherein the tip operating unit has a plurality of kinds, and the speed setting unit changes the operating speed for each kind of the tip operating unit that is provided in the working unit mounted to the main body portion and registers the set value of the operating speed for each kind in the storage unit.

5. The medical manipulator system according to claim 1, wherein the controller includes a storage unit that stores a set value of the operating speed of the tip operating unit through the speed setting unit.

6. The medical manipulator system according to claim 5, wherein the tip operating unit has a plurality of kinds, and the speed setting unit changes the operating speed for each kind of the tip operating unit provided in the working unit mounted to the main body portion and registers the set value of the operating speed for each kind in the storage unit.

7. The medical manipulator system according to claim 1, wherein the controller individually changes the operating speed of the tip operating unit of each of the plurality of medical manipulators.

8. The medical manipulator system according to claim 1, wherein:
the speed setting unit includes a display portion that displays the set speeds of the tip operating unit.

9. The medical manipulator system according to claim 1, wherein the speed setting unit displays the operating speed of the rotation operation and the swing operation for the tip operating unit for each medical manipulator connected to the at least two connectors.

10. The medical manipulator system according to claim 1, wherein connection and disconnection of each medical manipulator to the controller is detected, and upon connection of each medical manipulator to the controller its type and operating speed are displayed.

11. The medical manipulator system according to claim 1, wherein the speed setting unit selectively displays the operating speed for the tip operating unit for each medical manipulator based on the user-selected memory folder and each medical manipulator's detected type.

12. The medical manipulator system according to claim 1, wherein connection and disconnection of each medical manipulator to the controller is detected, and upon connection of each medical manipulator to the controller its type and operating speed are displayed; and
the speed setting unit selectively displays the operating speed for the tip operating unit for each medical manipulator based on the user-selected memory folder and each medical manipulator's detected type.

13. A medical manipulator system comprising:
a plurality of medical manipulators, each of said medical manipulators including:
a main body portion that includes drive shafts which are rotated by actuators and an input unit which drives the actuators; and
a working unit that includes driven shafts which are rotatably driven by the main body drive shafts, a tip operating unit which is operated by the rotation of the driven shafts, and a shaft which is provided at a tip of the tip operating unit, and wherein the shaft is attachable to and detachable from the main body portion;
a controller including at least two connectors, each of which is configured to be connected to one of the plurality of medical manipulators, wherein the controller independently and simultaneously controls the actuators of the medical manipulators based on an input operation to the input unit;
wherein the actuators are driven based on the input operation to the input unit, and the tip operating unit performs at least a rotation operation along an axial direction or a swing operation that crosses the axial direction;
wherein the controller changes driving speeds of the actuators, and includes a speed setting unit that sets an operating speed of a rotation operation or a swing operation for each of the medical manipulators, and that changes the operating speed of the rotation operation or the swing operation of the tip operating unit according to a stored preference of one of a plurality of predetermined users; and
wherein the speed setting unit simultaneously displays, based on a user-selected memory folder, the operating speed of the rotation operation or the swing operation for the tip operating unit for each medical manipulator connected to the at least two connectors and displays the set driving speed of the actuators before a change of speed and after the change of speed such that the user can view and confirm changing the set speed, and such that the speed of each medical manipulator connected to the at least two connectors can be simultaneously changed.

14. The medical manipulator system according to claim 13, wherein the tip operating unit performs the rotation operation and the swing operation, and the speed setting unit individually changes the operating speeds of the rotation operation and the swing operation, respectively.

15. The medical manipulator system according to claim 14, wherein the controller includes a storage unit that stores a set value of the operating speed of the tip operating unit through the speed setting unit, and a combination of the set values of the operating speed of the rotation operation and the swing operation can be registered in a plurality of combinations in the storage unit.

16. The medical manipulator system according to claim 15, wherein the tip operating unit has a plurality of kinds, and the speed setting unit changes the operating speed for each kind of the tip operating unit that is provided in the working unit mounted to the main body portion and registers the set value of the operating speed for each kind in the storage unit.

17. The medical manipulator system according to claim 13, wherein the controller includes a storage unit that stores a set value of the operating speed of the tip operating unit through the speed setting unit.

18. The medical manipulator system according to claim 17, wherein the tip operating unit has a plurality of kinds, and the speed setting unit changes the operating speed for each kind of the tip operating unit that is provided in the working unit mounted to the main body portion and registers the set value of the operating speed for each kind in the storage unit.

19. The medical manipulator system according to claim 13, wherein:
the speed setting unit includes a display portion that displays the set speeds of the tip operating unit.

* * * * *